US010330556B2

(12) United States Patent
Furumoto et al.

(10) Patent No.: US 10,330,556 B2
(45) Date of Patent: Jun. 25, 2019

(54) ENVIRONMENTAL TESTING DEVICE

(71) Applicant: Shinwa Controls Co., Ltd., Kawasaki-Shi (JP)

(72) Inventors: Hideaki Furumoto, Kawasaki (JP); Tomoaki Ito, Kawasaki (JP)

(73) Assignee: Shinwa Controls Co., Ltd., Kawasaki-Shi (JP)

(*) Notice: Subject to any disclaimer, the term of this patent is extended or adjusted under 35 U.S.C. 154(b) by 0 days.

(21) Appl. No.: 15/578,401

(22) PCT Filed: Jun. 6, 2016

(86) PCT No.: PCT/JP2016/066777
§ 371 (c)(1),
(2) Date: Nov. 30, 2017

(87) PCT Pub. No.: WO2016/195111
PCT Pub. Date: Dec. 8, 2016

(65) Prior Publication Data
US 2018/0217019 A1    Aug. 2, 2018

(30) Foreign Application Priority Data
Jun. 5, 2015    (JP) ................................ 2015-114932

(51) Int. Cl.
*G01M 3/00*    (2006.01)
*F25B 7/00*    (2006.01)
*G01N 17/00*    (2006.01)

(52) U.S. Cl.
CPC ............... *G01M 3/002* (2013.01); *F25B 7/00* (2013.01); *G01N 17/00* (2013.01); *F25B 2400/06* (2013.01)

(58) Field of Classification Search
CPC ....... G01M 3/002; F25B 7/00; F25B 2400/06; G01N 17/00
See application file for complete search history.

(56) References Cited

U.S. PATENT DOCUMENTS

2006/0225876 A1    10/2006    Shimizu
2009/0205344 A1    8/2009    Ascani
2012/0023979 A1    2/2012    Taylor et al.

FOREIGN PATENT DOCUMENTS

EP    1 828 693    9/2007
EP    1 828 693 B1    4/2008
(Continued)

OTHER PUBLICATIONS

HyTReC: Hydrogen Energy Product Research and Test Center, p. 5, upper left column [online], [retrieved on Jun. 5, 2015], Internet <URL: http://www.hytrec.jp/pdf/H26panfu.compressed.pdf>.
(Continued)

*Primary Examiner* — Ana M Vazquez
(74) *Attorney, Agent, or Firm* — Burr & Brown, PLLC

(57) ABSTRACT

An environmental testing apparatus includes a chamber, a cooling unit including a cooling apparatus of a brine that cools the inside of the chamber, a heating unit and a control apparatus. The cooling apparatus includes: a high temperature side cooling circuit including a high temperature side compressor, condenser, high temperature side expansion valve and cascade condenser connected in this order to circulate a high temperature side heating medium; and a low temperature side cooling circuit including a low temperature side compressor, cascade condenser, low temperature side expansion valve and evaporator connected in this order to circulate a low temperature side heating medium. The low temperature side heating medium is cooled by the high temperature side heating medium in the cascade condenser, while the brine is cooled by the low temperature side heating medium in the evaporator. The control apparatus controls a temperature inside the chamber to between −67.5° C. and 127.5° C.

15 Claims, 10 Drawing Sheets

(56)     References Cited

FOREIGN PATENT DOCUMENTS

| | | |
|---|---|---|
| EP | 3 306 228 A1 | 4/2018 |
| JP | S52-101753 A1 | 8/1977 |
| JP | S59-162645 U | 10/1984 |
| JP | H02-300101 A1 | 12/1990 |
| JP | H10-026485 A1 | 1/1998 |
| JP | H10-197077 A1 | 7/1998 |
| JP | 2004-271534 A1 | 9/2004 |
| JP | 2006-284063 A1 | 10/2006 |
| JP | 2006-285454 A1 | 10/2006 |
| JP | 2006-292204 A1 | 10/2006 |
| JP | 2007-240105 A1 | 9/2007 |
| JP | 2008-075919 A1 | 4/2008 |
| JP | 2008-524624 A1 | 7/2008 |
| JP | 2009-109065 A1 | 5/2009 |
| JP | 2011-033295 A1 | 2/2011 |
| JP | 2013-024453 A1 | 2/2013 |
| JP | 2015-068630 A1 | 4/2015 |
| WO | 2014/076891 A1 | 5/2014 |
| WO | 2016-195111 A1 | 12/2016 |

OTHER PUBLICATIONS

English translation of International Preliminary Report on Patentability (Chapter I) (Application No. PCT/JP2016/066777) dated Dec. 14, 2017, 10 pages.
English translation of International Preliminary Report on Patentability (Chapter I) (Application No. PCT/JP2017/001897) dated Aug. 9, 2018, 13 pages.
International Search Report and Written Opinion (Application No. PCT/JP2016/066777) dated Aug. 30, 2016.
European Search Report (Application No. 16 80 3542.6) dated Mar. 14, 2019.

ENVIRONMENTAL TESTING DEVICE

FIELD OF THE INVENTION

The present invention relates to an environmental testing apparatus for subjecting an object to be tested, such as a hydrogen tank, to an environmental testing in a low temperature zone and a high temperature zone.

BACKGROUND ART

As a method of filling a hydrogen tank of a fuel cell vehicle with hydrogen as fuel, there are known a method of compressing hydrogen at a high pressure and filling the hydrogen into a hydrogen tank, a method of liquefying hydrogen and filling the hydrogen into a hydrogen tank, and the like. When hydrogen is compressed at a high pressure and is filled into a hydrogen tank, the higher the pressure at which the hydrogen is compressed is, the more a filling amount of hydrogen can be increased, which can elongate a cruising distance of a fuel cell vehicle. On the other hand, as a pressure of hydrogen when it is supplied into a hydrogen tank and a pressure of the hydrogen filled therein increase, the hydrogen is more likely to leak during the supplying operation and to leak outside after the filling operation. Thus, a hydrogen tank capable of suitably preventing leakage of hydrogen during a supplying operation and after a filling operation has been conventionally developed.

A degree of the aforementioned leakage of hydrogen from a hydrogen tank may vary depending on an environment. In addition, there is a possibility that an amount of hydrogen, which can be filled into a hydrogen tank from outside, and an amount of hydrogen, which can be supplied from the inside of a hydrogen tank to the outside, might vary depending on an environment. Thus, in the general development of a hydrogen tank, environmental tests are carried out under various conditions such as a low temperature zone, a high temperature zone and so on. Various apparatuses have been conventionally used as a test apparatus for carrying out an environmental test of a hydrogen tank. For example, Non-Patent Document 1 discloses a test apparatus including a relatively large chamber in which a hydrogen tank environmental test can be carried out within a temperature zone of between −40° C. and 85° C.

Non-Patent Document 1: HyTReC: Hydrogen Energy Product Research and Test Center, page 5, upper left column [online], [retrieved on Jun. 5, 2015], Internet <URL:http://www.hytrec.jp/pdf/H26panfu.compressed.pdf>

SUMMARY OF THE INVENTION

A fuel cell vehicle is expected to become widely used in a lot of regions. In order to achieve this, it is necessary to subject a hydrogen tank to environmental tests conceiving various environments. Due to the relatively wide space in the chamber, the testing apparatus of the above Non-Patent Document 1 is advantageous in that environmental tests for a plurality of hydrogen tanks can be simultaneously carried out, and in that an environmental test for hydrogen tanks of various sizes can be carried out, for example.

However, it cannot be said that the temperature zone of between −40° C. and 85° C., within which an environmental test can be carried out, is sufficient enough, in consideration of environmental tests conceiving various environments. Thus, it is desired that environmental tests can be carried out in a broader temperature zone. However, in a testing device of such a kind, when a space in a chamber, whose temperature is to be controlled is enlarged, there occurs a problem in that control of a test temperature down to a significantly low temperature zone becomes difficult.

The present invention has been made in view of the above circumstances. The object of the present invention is to provide an environmental testing apparatus capable of sufficiently ensuring a space in a chamber in which an object to be tested is accommodated, and of controlling a temperature in the space within a broad temperature zone, in particular, down to a significantly low-temperature zone, whereby it is possible to subject an object to be tested to an environmental testing sufficiently considering various environments.

An environmental testing apparatus of the present invention comprises: a chamber that accommodates an object to be tested; a cooling unit including: a brine circulation apparatus that has a brine circulation path a part of which is located in the chamber, and circulates a brine in the brine circulation path; and a cooling apparatus that cools the brine in a part of the brine circulation path, which is located outside the chamber; a heating unit including a heater located in the chamber; and a control apparatus that controls the cooling unit and the heating unit; wherein: the cooling apparatus includes: a high temperature side cooling circuit in which a high temperature side compressor, a condenser, a high temperature side expansion valve and a cascade condenser are connected in this order by pipes so as to circulate a high temperature side heat medium; and a low temperature side cooling circuit in which a low temperature side compressor, the cascade condenser, a low temperature side expansion valve and an evaporator are connected in this order by pipes so as to circulate a low temperature side heating medium; with the low temperature side heating medium being configured to be cooled by the high temperature side heating medium in the cascade condenser, while the brine being configured to be cooled by the low temperature side heating medium in the evaporator; and the control apparatus is configured to control the cooling unit and the heating unit so as to control a temperature inside the chamber within a temperature zone of between −67.5° C. and 127.5° C.

According to the environmental testing apparatus of the present invention, since the binary type cooling apparatus including the high temperature side cooling circuit and the low temperature side cooling circuit is used, even when a relatively wide space is ensured in the chamber, a temperature in the chamber can be controlled down to a significantly low temperature zone, specifically, about −60° C. On the other hand, in a high temperature zone, a temperature in the chamber can be controlled up to about 120° C. by the heating unit. Thus, it is possible to sufficiently ensure a space in the chamber in which an object to be tested is accommodated, and to control a temperature in the space within a broad temperature zone, in particular, down to a significantly low temperature zone, whereby it is possible to subject an object to be tested to an environmental test sufficiently considering various environments.

Specifically, an internal volume of the chamber may be not less than 10 m$^3$ and not more than 20 m$^3$. In this case, it is possible to ensure a sufficient space in which environmental tests for a plurality of objects to be tested can be simultaneously carried out, and an environmental test for objects to be tested of various sizes can be carried out. When the internal volume of the chamber is within the aforementioned range (not less than 10 m$^3$ and not more than 20 m$^3$), the space in the chamber can be controlled at a desired temperature, without ensuring an excessively large output of the binary type cooling apparatus. Thus, since a temperature in the chamber can be controlled over a broad temperature zone by a relatively simple structure while sufficiently ensuring a space in the chamber 10, usefulness can be ensured.

In this case, when the brine circulation apparatus cools the space in the chamber, the brine circulation apparatus may be configured to cool the space in the chamber at a cooling capacity of 4 kW, by circulating the brine in the brine circulation path at a flow rate within a range of between 80 L/min and 160 L/min.

According to this structure, when the internal volume of the chamber is not less than 10 $m^3$ and not more than 20 $m^3$, since the brine is circulated within a range of between 80 L/min and 160 L/min so that the space in the chamber is cooled at a cooling capacity of 4 kW, a temperature in the chamber can be controlled down to about −60° C. for relatively a short period of time. Thus, usefulness can be improved.

In addition, a part of the brine circulation path, which is located in the chamber, may include a plurality of pipe parts each of which extends along the same direction; and when seen in a section perpendicular to an extension direction of the pipe part, the plurality of pipe parts may be disposed in a staggered arrangement (hound's tooth-like arrangement).

According to this structure, a layout of the pipe parts constituting a part of the brine circulation path located in the chamber can be made compact, whereby a wide installation space, in which an object to be tested can be placed, can be ensured in the chamber. In addition, since a gas in the chamber can be brought into contact with a wide area of the pipe parts, a heat exchange rate can be improved.

In addition, in this case, the part of the brine circulation path, which is located in the chamber, may be composed of a first pipe group and a second pipe group; each of the first pipe group and the second pipe group may include the plurality of pipe parts; the first pipe group may be located on one horizontal side in the chamber, while the second pipe group may be located the other horizontal end in the chamber; and the installation space for the object to be tested may be formed between the first pipe group and the second pipe group.

According to this structure, the wide installation space between the first pipe group and the second pipe group can be ensured. In addition, since a temperature in the installation space is controlled from both the horizontal sides, a uniform temperature distribution can be obtained.

In addition, in this case, in the chamber, a first cover member that covers the first pipe group from the installation space side may be located, and a second cover member that covers the second pipe group from the installation space side may be located.

According to this structure, the pipe parts included in the first pipe group and the second pipe group can be protected by the first cover member and the second cover member. The installation space is positioned between the first cover member and the second cover member.

In addition, in this case, a fan may be located above the installation space in the chamber; a third cover member that covers the fan from the installation space side may be located in the chamber; and the fan may be configured to blow air toward the third cover member.

According to this structure, by driving the fan, a dispersion in temperature distribution of the space in the chamber can be restrained. In addition, since the third cover member restrains that the air blown from the fan comes into direct contact with the object to be tested placed in the installation space, a temperature condition of the object to be tested can be made stable. Further, the fan can be protected by the third cover member.

In addition, in this case, the heater may be located above the fan.

According to this structure, the heater can be protected by the third cover member.

In addition, An environmental testing apparatus of the present invention comprises: a chamber that accommodates an object to be tested; a cooling unit and a heating unit, which are for controlling a temperature in the chamber; and a control apparatus that controls the cooling unit and the heating unit; wherein: the cooling unit includes a low temperature side refrigerating apparatus and a low temperature side brine circulation apparatus; the low temperature side refrigerating apparatus constituting a binary refrigerating apparatus includes: a first low temperature side refrigerating circuit in which a first low temperature side compressor, a first low temperature side condenser, a first low temperature side expansion valve and a first low temperature side evaporator are connected in this order so as to circulate a first low temperature side coolant; and a second low temperature side refrigerating circuit in which a second low temperature side compressor, a low temperature side condenser, a second low temperature side expansion valve and a second low temperature side evaporator are connected in this order so as to circulate a second low temperature side coolant; with the first low temperature side condenser and the second low temperature side evaporator constituting a cascade condenser in which they can be heat-exchanged with each other; the low temperature side brine circulation apparatus includes: a low temperature side brine circulation path for circulating a low temperature side brine; and a low temperature side heating part constituting a part of the low temperature side brine circulation path and capable of heating the low temperature side brine received therein; a part of the low temperature side refrigerating circuit, which is located on the downstream side of the first low temperature side expansion valve and on the upstream side of the first low temperature side evaporator, and a part of the low temperature side brine circulation path, which is located on the downstream side of the low temperature side heating part, constituting a refrigerating capacity adjusting mechanism in which they can be heat-exchanged with each other; and the first low temperature side evaporator being located in the chamber; and the control apparatus is configured to control the cooling unit and the heating unit so as to control a temperature inside the chamber within a temperature zone of between −67.5° C. and 127.5° C.

According to the environmental testing apparatus, in the cooling unit, the first low temperature side coolant can be heated by the low temperature side brine at the part on the upstream side of the first low temperature evaporator in the first low temperature side refrigerating circuit of the low temperature side refrigerating apparatus. At this time, a refrigerating capacity of the first low temperature side evaporator can be adjusted depending on a heating capacity of the low temperature side brine. Thus, the refrigerating capacity of the first low temperature side refrigerating circuit can be widely adjusted in a simple manner, without operating any constituent element of the low temperature refrigerating circuit.

By giving the cooling unit and the heating unit different temperature control ranges, a sufficiently broad temperature control range from a low temperature to a high temperature can be ensured.

In addition, the heating unit may include a heating side refrigerating apparatus and a heating side brine circulation apparatus; the heating side refrigerating apparatus may include: a heating side refrigerating circuit in which a heating side compressor, a heating side condenser, a heating side expansion valve and a heating side evaporator are connected in this order so as to circulate a heating side coolant; an injection circuit including: an injection flow path that communicates a part of the heating side refrigerating circuit, which is located on the downstream side of the heating side condenser and on the upstream side of the heating side expansion valve, and a part of the heating side refrigerating circuit, which is located on the downstream side of the heating side evaporator and on the upstream side of the heating side compressor, such that the heating side coolant can flow therethrough; and an injection valve capable of adjusting a flow rate of the heating side coolant; and a hot gas circuit including: a hot gas flow path that communicates a part of the heating side refrigerating circuit, which is located on the downstream side of the heating side compressor and on the upstream side of the heating side condenser, and a part of the injection flow path, which is located on the downstream side of the injection valve, such that the heating side coolant can flow therethrough; and a hot gas valve capable of adjusting a flow rate of the heating side coolant flowing through the hot gas flow path; and the heating side brine circulation apparatus may include: a heating side brine circulation path for circulating a heating side brine; a heating unit side heating part constituting a part of the heating side brine circulation path and capable of heating the heating side brine received therein; and a loading part constituting a part of the heating side brine circulation path on the downstream side of the heating unit side heating part and located in the chamber; a part of the heating side brine circulation path and the heating side evaporator of the heating side refrigerating apparatus constituting a heating capacity adjusting heat exchanger in which they can be heat-exchanged with each other.

In this case, the heating side coolant condensed by the heating side condenser can be passed through the injection circuit without allowing it to flow into the heating side evaporator, so as to be bypassed to the downstream side of the heating side evaporator, as well as the high-temperature heating side coolant ejected by the heating side compressor can be passed through the hot gas circuit so as to be bypassed to the downstream side of the heating side evaporator. Thus, a flow rate of the heating side coolant flowing into the heating side evaporator can be controlled, whereby a refrigerating capacity outputted by the heating side evaporator can be flexibly adjusted. At this time, since the heating side coolant flowing into the heating side evaporator is not mixed with the high-pressure heating side coolant, the refrigerating capacity to be outputted can be made stable. In addition, by adjusting a ratio between the condensed heating side coolant bypassed through the injection circuit and the high-temperature heating side coolant bypassed through the hot gas circuit, the condition and temperature of the heating side coolant to flow into the heating side compressor can be easily controlled desirably. Thus, a stable temperature control can be performed while flexibly adjusting the refrigerating capacity. Thus, since a temperature of the heating side brine of the heating side brine circulation apparatus can be controlled by the stably adjusted refrigerating capacity outputted by the heating side refrigerating apparatus, whereby the heating capacity or the refrigerating capacity of the loading parts can be adjusted, the stable temperature control can be performed by means of the loading parts.

According to the present invention, it is possible to sufficiently ensure a space in the chamber in which an object to be tested is accommodated, and to control a temperature in the space within a broad temperature zone, in particular, down to a significantly low temperature zone, whereby it is possible to subject an object to be tested to environmental tests sufficiently considering various environments.

DETAILED DESCRIPTION OF THE INVENTION

Respective embodiments of the present invention will be described herebelow.

«First Embodiment»

Figure 1:
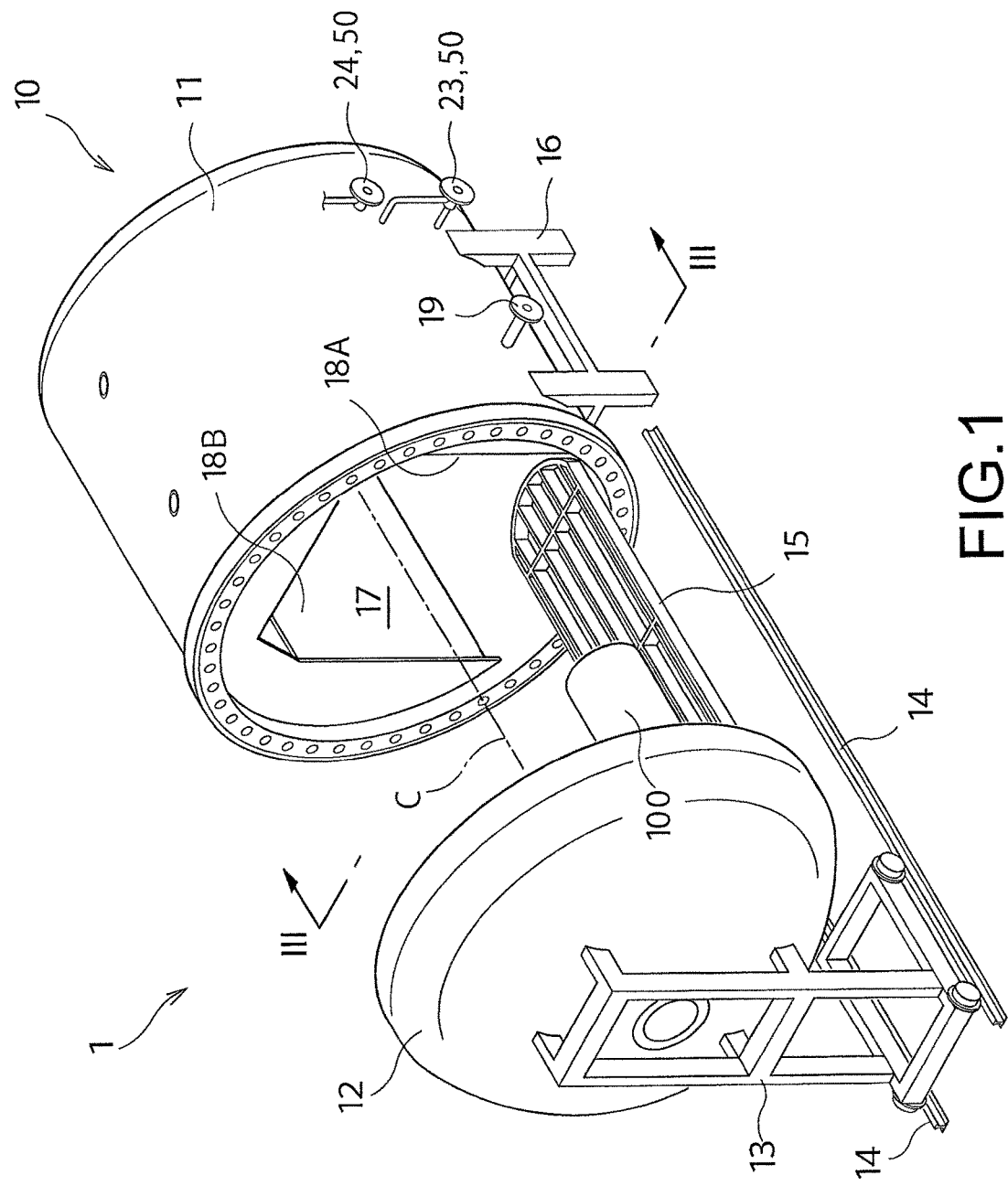
FIG. 1 is a perspective view of an environmental testing apparatus according to a first embodiment of the present invention.
Figure 2:
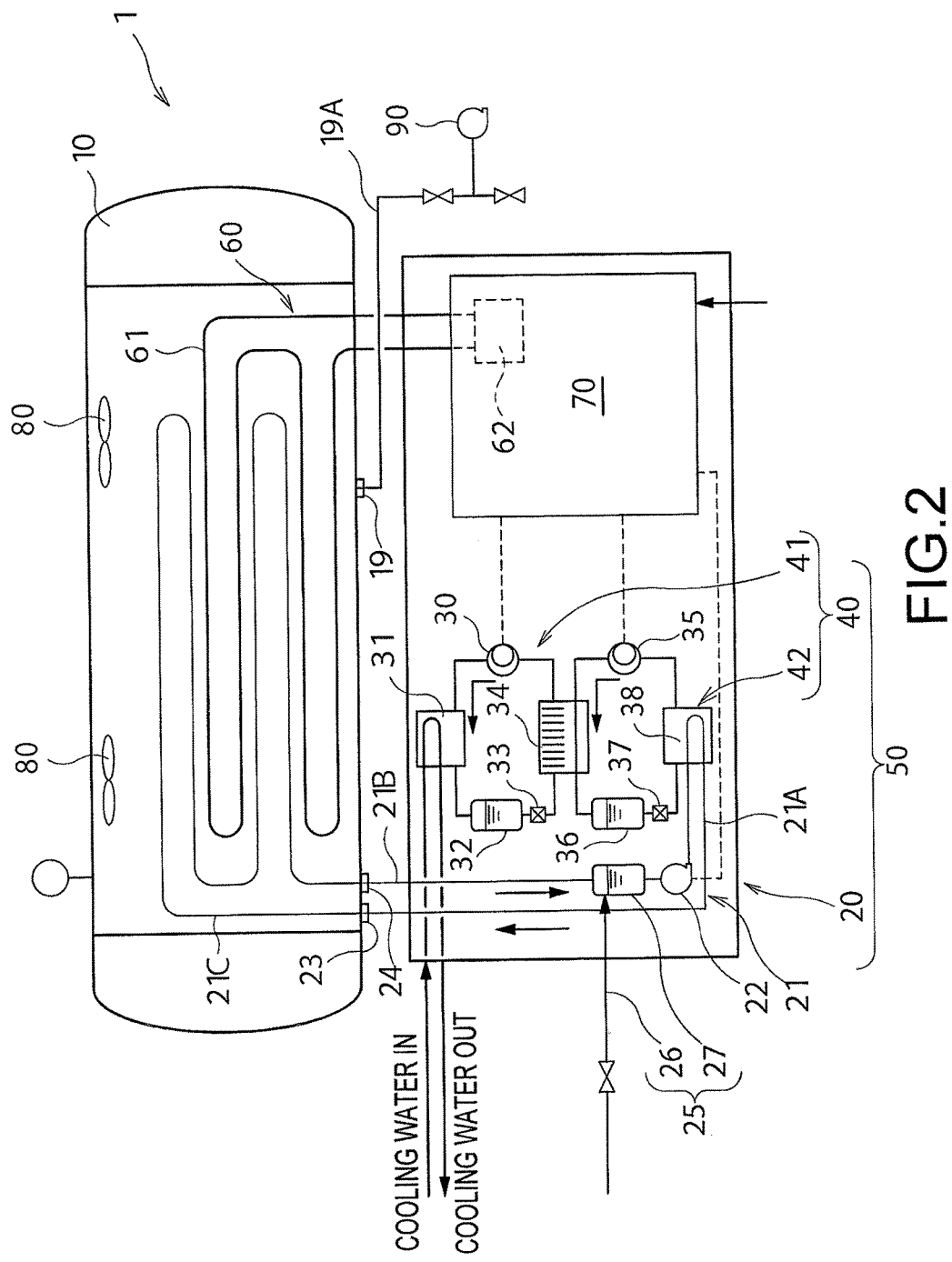
FIG. 2 is a view showing a circuit structure of the environmental testing apparatus shown in FIG. 1.

FIG. 1 is a perspective view of an environmental testing apparatus according to a first embodiment of the present invention. FIG. 2 is a view showing a circuit structure of the environmental testing apparatus shown in FIG. 1. As shown in FIGS. 1 and 2, the environmental testing apparatus 1 according to this embodiment includes a chamber 10 that accommodates an object 100 to be tested, such as a hydrogen tank, a cooling unit 50, a heating unit 60, and a control apparatus 70. In FIG. 1, the chamber 10 and the cooling unit 50 are only partially shown, for the sake of convenience of explanation.

As shown in FIG. 1, the chamber 10 in this embodiment has a cylindrical body part 11 with a bottom, and a discoid lid part 12 capable of opening and closing an opening of the body part 11. FIG. 1 shows an opened state of the chamber 10, in which the body part 11 is opened by the lid part 12. By closing the body part 11 with the lid part 12, the chamber 10 becomes a closed state from the opened state.

Figure 3:
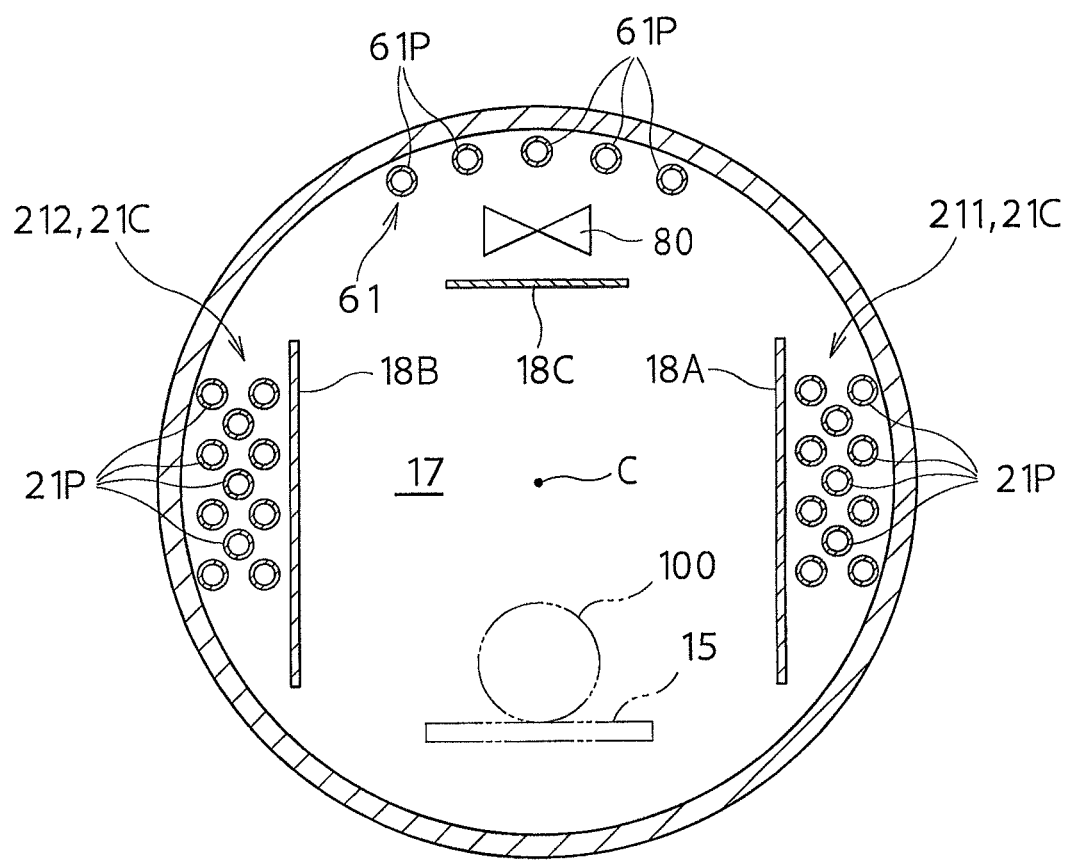
FIG. 3 is a longitudinal (vertical) sectional view of a chamber of the environmental testing apparatus shown in FIG. 1.

The body part 11 is installed on a floor surface through a pedestal 16, such that a central axis C of the body part 11 extends horizontally. FIG. 3 is a longitudinal (vertical) sectional view of the chamber 10 shown in FIG. 1. As shown in FIGS. 1 and 3, in this embodiment, the body part 11 includes therein a first cover member 18A, a second cover member 18B and a third cover member 18C. In the longitudinal (vertical) section view, the first cover 18A is located on one horizontal side. The second cover member 18B is located on the other horizontal side. The third cover member 18C is located above the first cover member 18A and the second cover member 18B, and between the first cover member 18A and the second cover member 18B in the horizontal direction.

The first cover member 18A and the second cover member 18B each have a plate-like shape, and are located to face each other with the central axis C therebetween in the horizontal direction perpendicular to the central axis C. In more detail, each of the first cover member 18A and the second cover member 18B extends in the up and down direction (vertical direction), and is located such that a gap is formed between a bottom end thereof and an inner circumferential surface of the body part 11. In this example, each of the bottom ends of the first cover member 18A and the second cover member 18B is located below the central axis C, more specifically, is located at a height position equivalent to a substantially mid position between the central axis C and the lowermost point of the inner circumferential surface of the body part 11. In addition, the first cover member 18A and the second cover member 18B extend along the central axis C from a point near the opening of the body part 11 up to a point near the bottom part of the cylindrical shape with the bottom.

The third cover member 18C has a plate-like shape, and is located above the central axis C so as to extend along the horizontal direction perpendicular to the central axis C. A gap is formed between an end of the third cover member 18C on the side of the first cover member 18A and an upper end of the first cover member 18A, while a gap is formed between an end of the third cover member 18C on the side of the second cover member 18B and an upper end of the second cover member 18B. The third cover member 18C also extends along the central axis C from a point near the opening of the body part 11 up to a point near the bottom part of the cylindrical shape with the bottom. An installation space 17, in which the object 100 to be tested is installed, is formed inside these respective cover members 18A to 18C.

In addition, in this embodiment, two fans 80 (see also FIG. 2) are located above the installation space 17. The third cover member 18C is located between the fans 80 and the installation space 17. The fans 80 are configured to blow air toward the third cover member 18C.

Returning to FIG. 1, the lid part 12 is equipped with a known seal member (not shown) at a position corresponding to an end edge on the side of the opening of the body part 11, whereby the opening of the body part 11 can be airtightly closed. Although not shown, a locking mechanism that holds the closed state of the body part 11 by the lid part 12 is disposed between the body part 11 and the lid part 12.

In this embodiment, as shown in FIG. 1, the lid part 12 is installed on a carriage 13 that is movable along a rail 14. The rail 14 is laid on the floor surface to extend along the direction of central axis C of the body part 11, from the side of the opening of the body part 11 to the outside. Thus, by moving the carriage 13 along the rail 14, the lid part 12 can be moved toward the body part 11 or the lid part 12 can be moved away from the body part 11.

In addition, in this embodiment, the lid part 12 is provided with a table 15 on which the object 100 to be tested is placed. The stage 15 is moved together with the lid part 12 by the carriage 13. When the body part 11 is closed by the lid part 12, the object 100 to be tested placed on the table 15 is configured to be positioned in the installation space 17 of the chamber 10.

In FIG. 3, the object 100 to be tested and the table 15 that are located in the installation space 17 of the chamber 10 are shown by the two-dot chain lines. In this embodiment, when located in the body part 11, the table 15 is positioned below the respective bottom ends of the first cover member 18A and the second cover member 18B. In the illustrated example, when the object 100 to be tested on the table 15 is located in the installation space 17 of the chamber 10, the respective cover members 18A to 18C are configured to surround the object 100 to be tested from above and from both sides in the horizontal direction perpendicular to the central axis C.

In addition, in the chamber 10 in this embodiment, the aforementioned body part 11 and the lid part 12 are both comprise a metal plate member and a heat insulation member stacked on the plate member. The metal plate member may be a plate member made of stainless steel (SUS316L) having a thickness of 12 mm. In addition, the heat insulation member may be a known heat insulation member having a thickness of 100 mm, such as a low foaming PET/PE sheet member.

In the state where the body part 11 is closed by the lid part 12, the chamber 10 has a substantially cylindrical outer shape with a diameter of 2400 mm and a length of 3400 mm. In this example, an internal volume of the chamber 10 is 15 $m^3$. Although the internal volume of the chamber 10 is 15 $m^3$ in this embodiment, the internal volume of the chamber 10 is preferably within a range of between 10 $m^3$ and 20 $m^3$. However, the internal volume of the chamber 10 is not particularly limited, and may be about 1.5 $m^3$ or about 25 $m^3$, for example.

In FIG. 1, the reference number 19 depicts a vent formed on a sidewall of the body part 11. Decompression means, such as a vacuum pump 90 (see FIG. 2), and compression means (not shown), such as a compressed hydrogen tank, are connected to the vent 19 through a pipe 19A. By means of the decompression means and the compression means, a pressure in the chamber 10 can be adjusted within a range of between 10 kPa and 150 kPa, for example.

Next, the cooling unit 50 is described. As shown in FIG. 2, the cooling unit 50 in this embodiment includes: a brine circulation apparatus 20 that has a brine circulation path 21 a part of which is located in the chamber 10, and circulates a brine in the brine circulation path 21; and a cooling apparatus 40 that cools the brine at a part of the brine circulation path 21, which is located outside the chamber 10.

The brine circulation apparatus 20 includes the aforementioned brine circulation path 21, a pump 22 that circulates the brine in the brine circulation path 21, and a brine-amount adjusting mechanism 25 that adjusts an amount of the brine in the brine circulation path 21. The brine-amount adjusting mechanism 25 has a brine tank 27 in which a predetermined amount of the brine is stored, and a brine supply path 26 that suitably supplies the brine tank 27 with a brine from outside. In this embodiment, a fluorine-based heating medium is used as a brine, but another brine may be used.

The brine circulation path 21 is described in detail. As shown in FIG. 2, the brine circulation path 21 has an upstream side flow path 21A and a downstream side flow path 21B which are located outside the chamber 10, and an intermediate flow path 21C disposed between the upstream side flow path 21A and the downstream side flow path 21B. The upstream side flow path 21A and the downstream side flow path 21B are connected through the aforementioned tank 27. The upstream side flow path 21A is provided with the aforementioned pump 22.

On the other hand, as shown in FIGS. 1 and 2, a brine inlet 23 is disposed on one end of both ends of the intermediate flow path 21C, and a brine outlet 24 is disposed on the other end. These brine inlet 23 and the brine outlet 24 are located outside the chamber 10. A part of the intermediate flow path 21, which is on the downstream side of the brine inlet 23 and on the upstream side of the brine outlet 24, is located in the chamber 10. The upstream side flow path 21A is connected to the brine inlet 23, and the downstream side flow path 21B is connected to the brine outlet 24. Thus, the brine circulation path 21 has a loop-like shape.

In this embodiment, as shown in FIG. 3, a part of the intermediate flow path 21C, which is located in the chamber 10, is composed of a first pipe group 211 and a second pipe group 212. Each of the first pipe group 211 and the second pipe group 212 includes a plurality of pipe parts 21P each of which extends in the same direction (in this embodiment, in the direction of the central axis C).

In this embodiment, in the chamber 10, the first pipe group 211 is located on one side in the horizontal direction perpendicular to the central axis C, and the second pipe group 212 is located on the other side in the horizontal direction perpendicular to the central axis C. The aforementioned installation space 17 is situated between the first pipe group 211 and the second pipe group 212. As shown in FIG. 3, in each of the first pipe group 211 and the second pipe group 212, when seen in a section perpendicular to an extension direction of the pipe part 21P, the pipe parts 21P are disposed in a staggered arrangement (hound's tooth-like arrangement). Namely, in this example, the plurality of pipe parts 21P arranged side by side in the up and down defines a row, and there are a plurality of such rows aligned in the horizontal direction. The plurality of pipe parts 21P are arranged such that a vertical position of a pipe part 21P included in one row of the adjacent rows in the horizontal direction is staggered from a vertical position of a pipe part 21P included in the other row. Each of the pipe part 21P is preferably provided with a fin in order to improve heat exchange rate.

The aforementioned first cover member 18A is positioned between the first pipe group 211 and the installation space 17, and extends along the first pipe group 211 so as to cover the first pipe group 211. In addition, the aforementioned second cover member 18B is positioned between the second pipe group 212 and the installation space 17, and extends along the second pipe group 212 so as to cover the second pipe group 212.

In this embodiment, the aforementioned cooling apparatus 40 is constituted as a binary type cooling apparatus (binary cooling apparatus). Namely, as shown in FIG. 2, the cooling apparatus 40 includes: a high temperature side cooling circuit 41 in which a high temperature side compressor 30, a water-cooled condenser 31, a high temperature side liquid receiver 32, a high temperature side expansion valve 33 and a cascade condenser 34 are connected in this order by pipes so as to circulate a high temperature side heating medium; and a low temperature side cooling circuit 42 in which a low temperature side compressor 35, the aforementioned cascade condenser 34, a low temperature side liquid receiver 36, a low temperature side expansion valve 37 and an evaporator 38 are connected in this order by pipes so as to circulate a low temperature side heating medium. The low temperature side heating medium is configured to be cooled by the high temperature side heating medium in the cascade condenser 34, while the brine is configured to be cooled by the low temperature side heating medium in the evaporator 38 of the low temperature side cooling circuit 42.

In order to improve a cooling efficiency of the brine, the cooling apparatus 40 in this embodiment employs, as the high temperature side heating medium, R410A which is a kind of hydrofluoro carbons, and, as the low temperature side heating medium, R23 which is a kind of hydrofluoro carbons. Combinations of coolants (high temperature side heating medium/low temperature side heating medium), which can be employed on the high temperature side and on the low temperature side, may be R22/R23, R404/R23, R403/R23, R410/R14, etc. Further, a coolant mixture may be employed as a heating medium.

Due to the employment of such a cooling apparatus 40, in this embodiment, it is possible to increase a flow rate of the brine circulating in the brine circulation path 21 and to sufficiently cool the brine, whereby the space in the chamber 10 can be effectively cooled. Specifically, when the space in the chamber 10 is cooled, the brine circulation apparatus 20 in this embodiment circulates the brine having a predetermined temperature at 120 L/min in the brine circulation path 21, so that the space in the chamber 10 is cooled at a cooling capacity of 4 kW. A cooling capacity of the brine may be varied by using an inverter. In addition, a cooling capacity of the brine may be varied by heat-controlling the brine in the brine circulation path 21 outside the chamber 10.

As shown in FIG. 2, the heating unit 60 in this embodiment includes a heater 61 located in the chamber 10, and a current control part 62 connected to the heater 61. Namely, the heating unit 60 in this embodiment is configured to heat the space in the chamber 10 by means of an electric heater. Specifically, the heating unit 60 in this embodiment heats the space in the chamber 10 at a warming capacity of 5 kW by means of the heater 61.

In this embodiment, as shown in FIG. 3, the heater 61 is located above the fans 80. In more detail, the heater 61 has a plurality of tubular portions 61P, and these tubular portions 61P are arranged side by side along an arcuate inner wall surface of the body part 11. Each tubular portion 61P of the heater 61 is preferably provided with a fin in order to improve a heat exchange rate.

In order to achieve a desired test environment, the control apparatus 70 controls the cooling unit 50 and the heating unit 60. To be specific, in this embodiment, the control apparatus 70 is configured to control the high temperature side compressor 30 of the cooling unit 50, the low temperature side compressor 35 thereof, the pump 22 of the brine circulation apparatus 20, and the heater 61 (current control part 62) of the heating unit 60.

In particular, in the environmental testing apparatus 1 in this embodiment, the control apparatus 70 controls the cooling unit 50 and the heating unit 60, such that a temperature in the chamber 10 is controlled at a desired set temperature within a temperature zone of between −67.5° C. and 127.5° C. In addition, in this embodiment, a temperature sensor and a pressure sensor, which are connected to the control apparatus 70, are provided in the chamber 10 so as to measure a temperature and a pressure in the chamber 10 on a real-time basis.

Next, an operation of this embodiment is described.

Upon start of an environmental test, when the body part 11 of the chamber 10 is closed by the lid part 12, a user releases the locking condition between the body part 11 and the lid part 12, and moves the carriage 13 along the rail 14 away from the body part 11. Thus, the lid member 12 is moved away from the opening of the body part 11, so that the table 15 mounted on the lid part 12 is exposed outside the chamber 10. Then, the user places the object 100 to be tested, such as a hydrogen tank, on the table 15, and fastens the object to be tested on the table 15 by a known a fastening tool (not shown).

Under this state, the user moves the carriage 13 along the rail 14 toward the body part 11, and closes the opening of the body part 11 of the chamber 10 by the lid part 12. Then, the user fastens the lid part 12 onto the body part 11 by using the above locking mechanism. Thus, the opening of the body part 11 is air-tightly closed by the lid part 12.

Then, when the user sets a desired test environment (test temperature) to the control apparatus 70, an environmental test is started. For example, when a test temperature of a low temperature zone, such as −60° C., is set, the control apparatus 70 firstly drives the high temperature side compressor 30 of the high temperature side cooling circuit 41, so as to start circulation of the high temperature side heating medium in the high temperature side cooling circuit 41 along the arrow direction shown in FIG. 2. To be specific, the high temperature side compressor 30 compresses the high temperature side heating medium to have a high temperature and a high pressure, and ejects the high temperature side heating medium toward the condenser 31. The condenser 31 condenses and liquefies the ejected high temperature side heating medium, by heat-exchanging it with cooling water supplied from outside. The condensed and liquefied high temperature side heating medium passes through the high temperature side expansion valve 33 via the high temperature side liquid receiver 32. At this time, the high temperature side expansion valve 33 decompresses the high temperature side heating medium. The decompressed high temperature side heating medium flows again into the high temperature side compressor 30 via the cascade condenser 34. This cooling cycle is repeated again.

In addition to the driving of the high temperature side compressor 30 of the high temperature side cooling circuit 41, the control apparatus 70 drives the low temperature side compressor 35 of the low temperature side cooling circuit 42, so as to start circulation of the low temperature side heating medium in the low temperature side cooling circuit 42 along the arrow direction shown in FIG. 2. To be specific, the low temperature side compressor 35 compresses the low temperature side heating medium to have a high temperature and a high pressure, and ejects the low temperature side heating medium toward the cascade condenser 34. The cascade condenser 34 condenses and liquefies the ejected low temperature side heating medium, by heat-exchanging it with the aforementioned high temperature side heating medium circulating in the high temperature side cooling circuit 41. The condensed and liquefied low temperature side medium passes through the low temperature side expansion valve 37 via the low temperature side liquid receiver 36. At this time, the low temperature side expansion valve 37 decompresses the low temperature side heating medium. The decompressed low temperature side heating medium flows again into the low temperature side compressor 35 via the evaporator 38. This cooling cycle is repeated again. In this manner, the low temperature side heating medium is cooled by the high temperature side heating medium in the cascade condenser 34, while the brine is cooled by the low temperature side heating medium in the evaporator 38 of the low temperature side cooling circuit 42.

Then, the control apparatus 70 drives the pump 22 of the brine circulation apparatus 20, so as to circulate the brine in the brine circulation path 21 along the arrow direction shown in FIG. 2. At this time, the brine is supplied by the pump 22 toward the evaporator 38 of the low temperature side cooling circuit 42 at a flow rate of 120 L/min. The supplied brine is heat-exchanged with the low temperature side heating medium through the evaporator 38 so as to be cooled. The cooled brine is supplied toward the chamber 10 so as to be supplied through the brine inlet 23 to the brine circulation path 21 located in the chamber 10, i.e., to the intermediate flow path 21C. The brine is heat-exchanged with a gas in the chamber 10 through the brine circulation path 21, at a cooling capacity of 4 Kw, so as to cool the inside of the chamber 10. Then, the brine, which has been heat-exchanged with the gas in the chamber 10, is returned to the outside of the chamber 10 through the brine outlet 24, so as to be supplied again to the evaporator 38. This cooling cycle is repeated again.

In this embodiment, while the inside of the chamber 10 is being cooled by the brine, the two fans 80 disposed on the inner wall of the chamber 10 are driven. Thus, the gas cooled by the brine circulation path 21 (first pipe group 211 and second pipe group 212), which is located between the first cover member 18A and the inner wall of the chamber 10, and between the second cover member 18B and the inner wall of the chamber 10, is diffused (convected) in the installation space 17. Thus, the installation space 17 is effectively cooled, as well as a dispersion in temperature distribution in the installation chamber 17 is restrained.

Along with the above cooling process, the gas in the chamber 10 contracts so that the pressure in the chamber 10 gradually decreases. Thus, when it is desired that the object 100 to be tested is tested under an atmospheric pressure, the user suitably opens and closes the vent 19 provided on the sidewall of the body part 11 of the chamber 10, such that the pressure in the chamber 10 is maintained at an atmospheric pressure. In this embodiment, the pressure in the chamber 10 is measured by the pressure sensor provided in the chamber 10 on a real-time basis, and a value thereof is displayed on a display part (not shown) disposed on the control apparatus 70.

Due to the above cooling process, the inventors confirmed that, although the chamber 10 had a relatively large internal volume of 15 m$^3$, the space in the chamber 10 could be cooled from the room temperature (25° C.) down to −60° C., in relatively a short period of time, i.e., 8 hours. In addition, the temperature of the chamber 10 is measured by the temperature sensor provided in the chamber 10 on a real-time basis, and a feedback control is performed based on a measured temperature. Thus, despite the fact that the chamber 10 is relatively large, the temperature of the chamber 10, in particular, the temperature of the installation space 17 can be maintained within an error rang of ±3° C. relative to −60° C. that is a set temperature.

After a desired period of test time has elapsed and the test of the object to be tested has ended, the user gives a command to the control apparatus 70 to stop the cooling process. Thus, the control apparatus 70 stops the driving of the high temperature side compressor 30, the low temperature side compressor 35, the pump 22 of the brine circulation apparatus 20, and the fans 80, respectively, so as to terminate the operation of the environmental testing apparatus 1.

On the other hand, when a high temperature zone, such as 120° C., is set in the control apparatus 70, the control apparatus 70 firstly controls the current control part 62 of the heating unit 60 so as to energize the heater 61 located in the chamber 10. Thus, the heater 61 generates heat, and a gas in the chamber 10 is heated at a warming capacity of 5 KW. While the heat 61 heats the inside of the chamber 10, the fans 80 disposed on the inner wall of the chamber 10 are driven. Thus, similarly to the test temperature in the low temperature zone, a dispersion in temperature distribution in the installation chamber 17 is restrained.

Along with the above heating process, the gas in the chamber 10 expands so that the pressure in the chamber 10 gradually increases. Thus, when it is desired that the object to be tested is tested under an atmospheric pressure, the user suitably opens and closes the vent 19 provided on the sidewall of the body part 11 of the chamber 10, such that the pressure in the chamber 10 is maintained at an atmospheric pressure.

Due to the above heating process, the inventors confirmed that, although the chamber 10 had a relatively large internal volume of 15 m$^3$, the space in the chamber 10 could be heated from the room temperature (25° C.) up to 120° C., in relatively a short period of time, i.e., 8 hours. In addition, similarly to the test temperature in the low temperature zone, the temperature in the chamber 10 is measured by the temperature sensor provided in the chamber 10 on a real-time basis, and a feedback control is performed based on a measured temperature. Thus, despite the fact that the chamber 10 is relatively large, the temperature in the chamber 10 can be maintained within an error rang of ±3° C. relative to 120° C. that is a set temperature.

The environmental testing apparatus 1 in this embodiment can carry out an environmental test in such a manner that the inside of the chamber 10 has a low pressure such as 10 kPa, regardless of a temperature in a test environment. In this case, as shown in FIG. 2, a vacuum pump 90 is connected to the vent 19. During the heating process or the cooling process, the vacuum pump 90 is suitably driven such that the inside of the chamber 10 is maintained at a pressure as low as 10 kPa.

Alternatively, the environmental testing apparatus 1 in this embodiment can carry out an environmental test in such a manner that the inside of the chamber 10 has a pressure higher that an atmospheric pressure, such as 150 kPa, regardless of a temperature in a test environment. In this case, in this embodiment, before the heating process or cooling process in the chamber 10 is started, a nitrogen supply source (not shown) is connected to the vent 19, and after the gas in the chamber 10 has been completely replaced with nitrogen, the pressure in the chamber 10 is maintained at 150 kPa.

According to the above-described environmental testing apparatus 1 in this embodiment, the use of the binary type cooling apparatus having the high temperature side circuit 41 and the low temperature side cooling circuit 42 makes it possible to control the temperature in the chamber to be lowered down to a significantly low temperature zone, specifically about −60° C., even though relatively a wide space is ensured in the chamber 10. On the other hand, in a high temperature zone, the temperature in the chamber 10 can be controlled by the heating unit 60 to be elevated up to about 120° C. Thus, it is possible to sufficiently ensure a space in the chamber in which an object to be tested is accommodated, and to control a temperature in the space within a broad temperature zone, in particular, down to a significantly low temperature zone, whereby it is possible to subject an object to be tested to an environmental testing sufficiently considering various environments.

Specifically, the internal volume of the chamber 10 in this embodiment is 15 m$^3$. Thus, it is possible to ensure a sufficient space in which environmental tests for a plurality of objects to be tested can be simultaneously carried out, and an environmental test for objects to be tested of various sizes can be carried out. In addition, when the internal volume of the chamber 10 has the aforementioned value, the space in the chamber 10 can be controlled at a desired temperature, without ensuring an excessively large output of the binary type cooling apparatus 40. Thus, according to this embodiment, since a temperature in the chamber 10 can be controlled over a broad temperature zone by a relatively simple structure while sufficiently ensuring a space in the chamber 10, usefulness can be ensured.

In addition, when the space in the chamber 10 is cooled, the brine circulation apparatus 20 in this embodiment is configured to circulate the brine in the brine circulation path 21 at 120 L/min, so as to cool the space in the chamber 10 at a cooling capacity of 4 kW. Thus, since the temperature in the chamber 10 can be controlled about −60° C. in relatively a short period of time, usefulness can be improved.

In addition, in this embodiment, the intermediate flow path 21C, which is a part of the brine circulation path 21 disposed in the chamber 10, has a plurality of the pipe parts 21P each of which extends along the same direction, and these pipe parts 21P are disposed in a staggered arrangement when seen in a section perpendicular to their extension direction. Thus, a layout of the pipe parts 21P constituting a part of the brine circulation path 21 located in the chamber 10 can be made compact, whereby the wide installation space 17 can be ensured in the chamber 10. In addition, since a gas in the chamber 10 can be brought into contact with a wide area of the pipe parts 21P, a heat-exchange rate can be improved.

More specifically, in this embodiment, the intermediate flow path 21C is composed of the first pipe group 211 and the second pipe group 212. Each of the first pipe group 211 and the second pipe group 212 includes the plurality of pipe parts 21P. The first pipe group 211 is located on one horizontal side, and the second pipe group 212 is located on the other horizontal side. The installation space 17 is formed between the first pipe group 211 and the second pipe group 212. Thus, the wide space 17 can be ensured between the first pipe group 211 and the second pipe group 212. Moreover, since a temperature in the installation space 17 is controlled from both the horizontal sides, a uniform temperature distribution can be obtained.

In addition, in this embodiment, the first cover member 18A extending along the first pipe group 211 is located between the first pipe group 211 and the installation space 17, while the second cover member 18B extending along the second pipe group 212 is located between the second pipe group 212 and the installation space 17. Thus, the pipe parts 21P included in the first pipe group 211 and the second pipe group 212 can be protected.

In addition, the fans 80 are located above the installation space 17 in the chamber 10, and the third cover member 18C is located between the fans 80 and the installation space 17. The fans 80 are configured to blow air toward the third cover member 18C. Thus, by driving the fans 80, a dispersion in temperature distribution in the space of the chamber 10 can be restrained. In addition, since the third cover member 18C restrains the air blown from the fans 80 from coming into direct contact with an object to be tested placed in the installation space 17, whereby a temperature condition of the objet to be tested can be made stable. Further, the fans 80 can be protected by the third cover member 18C.

In addition, in this embodiment, since the heater 61 is disposed above the fans 80, the heater 61 can be protected by the third cover member 18C.

The embodiment of the present invention has been described above, but the present invention is not limited to the aforementioned embodiment. For example, in the aforementioned embodiment, although the chamber 10 has a cylindrical shape, the present invention is not limited thereto. For example, the chamber 10 may have a parallelepiped shape, or may have a tubular shape with an elliptical longitudinal section.

In addition, in the aforementioned embodiment, although the brine is cooled by the binary type cooling apparatus 40, the brine may be cooled by a multistage type cooling apparatus having three or more stages.

«Second Embodiment»

Next, a second embodiment of the present invention is described. A constituent part of the second embodiment, which corresponds to the constituent part described in the first embodiment, has the same reference number. In addition, herebelow, description of the same constituent part of the second embodiment as the constituent part of the first embodiment is omitted. An environmental testing apparatus 2 in the second embodiment can control a temperature in the chamber 10 at a desired set temperature within a temperature zone of between −67.5° C. and 127.5° C. Structures of a cooling unit 50 and a heating unit 60 differ from those of the first embodiment.

Figure 4:
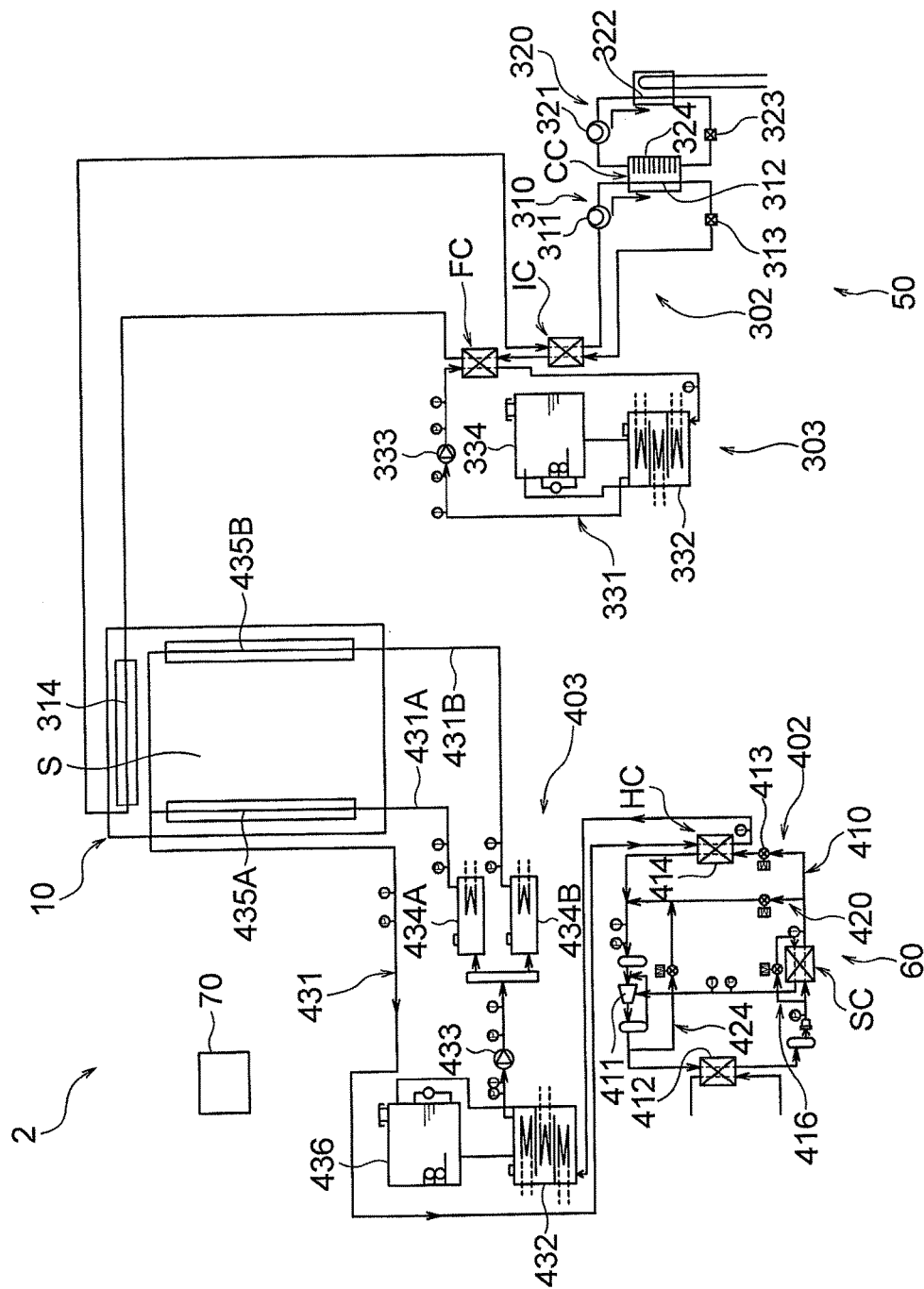
FIG. 4 is a view showing a schematic structure of the environmental testing apparatus according to a second embodiment of the present invention.

FIG. 4 is a view showing a schematic structure of the environmental testing apparatus 2 according to the second embodiment of the present invention. As shown in FIG. 4, the environmental testing apparatus 2 according to this embodiment includes a cooling unit 50, a heating unit 60 and a chamber 10 defining a space S whose temperature is to be controlled (temperature control space S). The environmental testing apparatus 2 can control, by the cooling unit 50 and the heating unit 60, a temperature of the temperature control space S at a desired temperature within a temperature control range from a low temperature to a high temperature. The respective structures of the environmental testing apparatus 2 are described in detail below.

<Cooling Unit>

As shown in FIG. 4, the cooling unit 50 in this embodiment includes a low temperature side refrigerating apparatus 302 and a low temperature side brine circulation apparatus 303. The cooling unit 50 can cool the temperature control space S, by adjusting a refrigerating capacity of the low temperature side refrigerating apparatus 302 by means of the low temperature side brine circulation apparatus 303.

The low temperature side refrigerating apparatus 302 in this embodiment is a binary refrigerating apparatus, and includes: a first low temperature side refrigerating circuit 310 in which a first low temperature side compressor 311, a first low temperature side condenser 312, a first low temperature side expansion valve 313 and a first low temperature side evaporator 314 are connected in this order so as to circulate a first low temperature coolant; and a second low temperature side refrigerating circuit 320 in which a second low temperature side compressor 321, a second low temperature side condenser 322, a second low temperature side expansion valve 323 and a second low temperature side evaporator 324 are connected in this order so as to circulate a second low temperature coolant. The first low temperature side condenser 312 and the second low temperature side evaporator 324 constitute a cascade condenser CC in which they can be heat-exchanged with each other.

In the first low temperature side refrigerating circuit 310, a first low temperature side coolant compressed by the first low temperature side compressor 311 flows into the first low temperature side condenser 312 constituting the cascade condenser CC so as to be condensed by the second low temperature side evaporator 324 of the second low temperature side refrigerating circuit 320. Thereafter, the first low temperature side coolant is decompressed by the first low temperature side expansion valve 313 to have a low temperature, and flows into the first low temperature side evaporator 314. In the illustrated example, the first low temperature side evaporator 314 is located in the chamber 10, and the first low temperature side coolant having flown into the first low temperature side evaporator 314 absorbs the heat of the temperature control space S and then flows into the first low temperature side compressor 311.

In this embodiment, a part of the first low temperature side refrigerating circuit 310, which is located on the downstream side of the first low temperature side expansion valve 313 and on the upstream side of the first low temperature side evaporator 314, and a part of the first low temperature side refrigerating circuit 310, which is located on the downstream side of the first low temperature side evaporator 314 and on the upstream side of the first low temperature side compressor 311, constitute an internal heat exchanger IC in which they can be heat-exchanged with each other. Thus, before the first low temperature side coolant, which has passed through the first low temperature side evaporator 314 to have an elevated temperature, is sucked into the first low temperature side compressor 311, the first low temperature side coolant can be cooled by the low-temperature first low temperature side coolant ejected by the first low temperature side expansion valve 313.

In the second low temperature side refrigerating circuit 320, the a second low temperature side coolant, which has absorbed the heat of the first low temperature side coolant in the cascade condenser CC, is compressed by the second low temperature side compressor 321. The compressed second low temperature side coolant flows into the second low temperature side condenser 322, and is condensed by, e.g., cooling water flowing in the second low temperature side condenser 322. Thereafter, the second low temperature side coolant is decompressed by the second low temperature side expansion valve 323 to have a low temperature, and flows into the second low temperature side evaporator 324 constituting the cascade condenser CC to cool the first low temperature side coolant having flown into the first low temperature side condenser 312.

The low temperature side brine circulation apparatus 303 includes a low temperature side brine circulation path 311 for circulating a low temperature side brine, a low temperature side heating part 332 constituting a part of the low temperature side brine circulation path 331 and capable of heating the low temperature side brine received therein, a low temperature side pump 333 constituting a part of the low temperature side brine circulation path 331 and giving a driving force for circulating the low temperature side brine in the low temperature side brine circulation path 331, and a low temperature side brine tank 334 connected to the low temperature side heating part 332.

In the illustrated example, when the low temperature side brine is circulated in the clockwise direction by the driving of the low temperature side pump 333 in the low temperature side brine circulation path 331, the low temperature side heating part 332 can heat the low temperature side brine received therein along with the circulation of the low temperature side brine, at a desired heating amount. The low temperature side heating part 332 has a case part into which the low temperature side brine flows and a heater disposed in the case part, and is capable of adjusting a heating capacity of the low temperature side brine by adjusting a heating amount of the heater. In this embodiment, the low temperature side heating part 332 can heat the low temperature side brine up to a temperature higher than a temperature of the first low temperature side coolant which has been decompressed by the first lower temperature side expansion valve 313 and heat-exchanged in the internal heat exchanger IC. The low temperature side brine is stored in the low temperature side brine tank 334, and an air layer is formed between a liquid level of the stored low temperature side brine and an upper wall of the low temperature side brine tank 334. The case part of the low temperature side heating part 332 fluidically communicates the air layer part in the low temperature side brine tank 334 and a liquid layer part of the low temperature side brine.

In this embodiment, a part of the first low temperature side refrigerating circuit 310, which is located on the downstream side of the first low temperature side expansion valve 313 and on the upstream side of the first low temperature side evaporator 314, and a part of the low temperature side brine circulation path 331, which is located on the downstream side of the low temperature side heating part 332, constitute a refrigerating capacity adjusting mechanism FC in which they can be heat-exchanged with each other. In the illustrated example, the refrigerating capacity adjusting mechanism FC is located on the downstream side of the internal heat exchanger IC in a direction along which the first low temperature side coolant flows. Namely, the internal heat exchange IC is located on the upstream side of the refrigerating capacity adjusting mechanism FC in the direction along which the first low temperature side coolant flows. To be more specific, in a part where the first low temperature side coolant ejected from the first low temperature side expansion valve 313 in the first low temperature side refrigerating circuit 310 reaches the first low temperature side evaporator 314, the internal heat exchanger IC is located on the upstream side of the refrigerating capacity adjusting mechanism FC. Thus, in the part of the first low temperature side refrigerating circuit 310 of the low temperature side refrigerating apparatus 302, which is on the upstream side of the first low temperature side evaporator 314, the first low temperature side coolant can be heated by the brine.

<Heating Unit>

Next, the heating unit 60 is described. As shown in FIG. 4, the heating unit 60 according to this embodiment has a heating side refrigerating apparatus 402 and a heating side brine circulation apparatus 403. In the heating unit 60, the heating side brine circulation apparatus 403 can heat or cool a temperature of the temperature control space S. When the heating capacity or refrigerating capacity of the heating side brine circulation apparatus 403 is adjusted, the heating side refrigerating apparatus 402 is configured to cool a heating side brine circulating in the heating side brine circulation apparatus 403.

Figure 5:
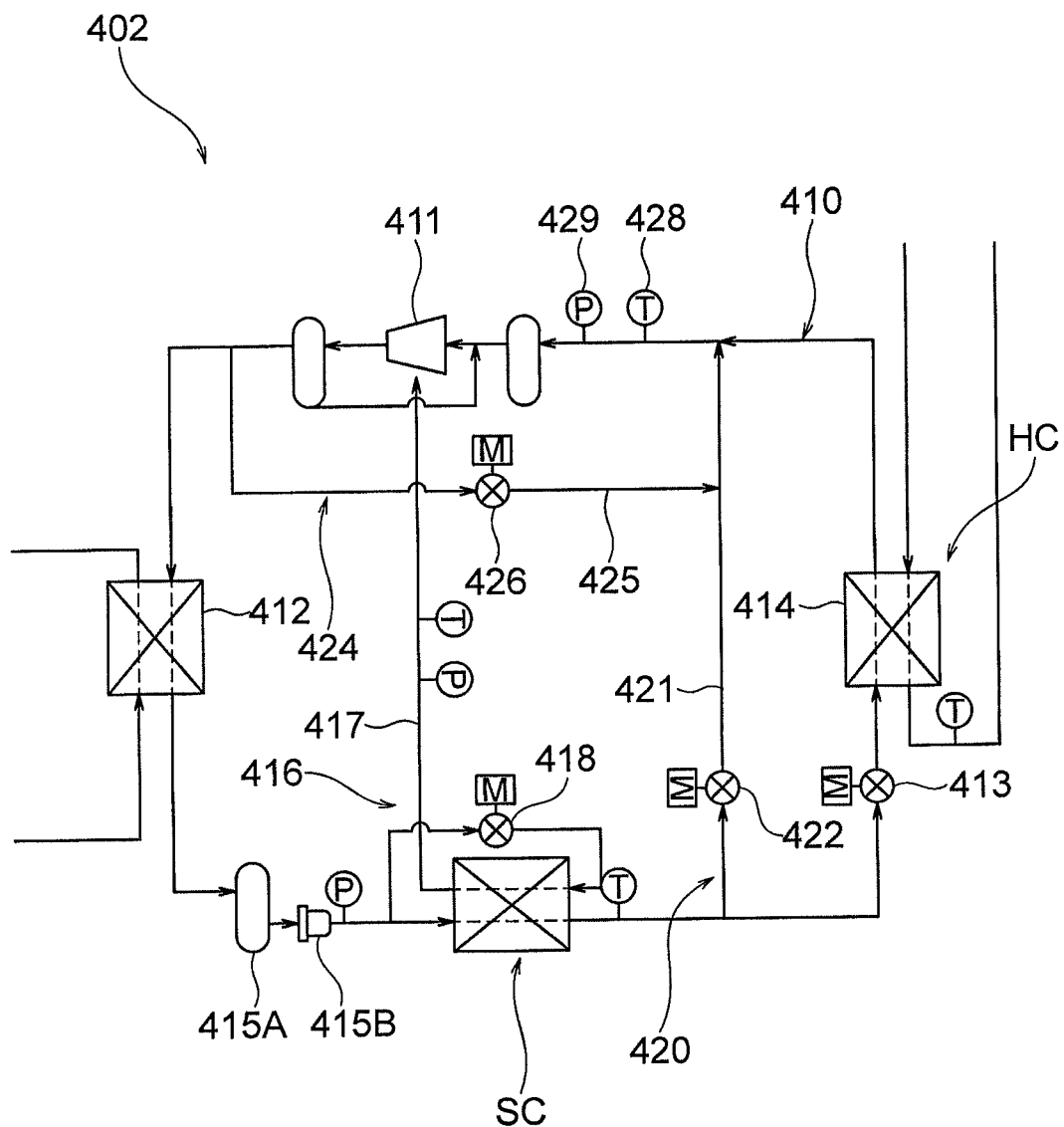
FIG. 5 is an enlarged view of a heating side refrigerating apparatus in a heating unit of the environmental testing apparatus shown in FIG. 4.

The heating side refrigerating apparatus 402 in this embodiment is a unitary type refrigerating apparatus, and includes: a heating side refrigerating circuit 410 in which a heating side compressor 411, a heating side condenser 412, a heating side expansion valve 413 and a heating side evaporator 414 are connected in this order so as to circulate a heating side coolant; an injection circuit 420 and a hot gas circuit 424 which are provided for bypassing the heating side coolant flowing through the heating side refrigerating circuit 410; and a supercooling circuit 416 for supercooling the heating side coolant flowing through the heating side refrigerating circuit 410. FIG. 5 is an enlarged view of the heating side refrigerating apparatus 402. Herebelow, the respective structures of the heating side refrigerating apparatus 402 are described in detail, with reference to FIG. 5.

A basic coolant flow in the heating side refrigerating circuit 410 shown in FIG. 5 is as follows. A heating side coolant compressed by the heating side compressor 411 flows into the heating side condenser 412. The heating side coolant having flown into the heating side condenser 412 is condensed by cooling water, for example. Thereafter, the heating side coolant is decompressed by the heating side expansion valve 413 to have a low temperature, and then flows into the heating side evaporator 414. The coolant having flown into the heating side evaporator 414 is heat-exchanged, and then flows into the heating side compressor 411. As described in detail below, the heating side refrigerating apparatus 402 in this embodiment is configured to cool the heating side brine circulating in the heating side brine circulation apparatus 403, by means of the heating side evaporator 414.

The injection circuit 420 includes: an injection flow path 421, which communicates (connects) a part of the heating side refrigerating circuit 410, which is located on the downstream side of the heating side condenser 412 and on the upstream side of the heating side expansion valve 413, and a part of the heating side refrigerating circuit 410, which is located on the downstream side of the heating side evaporator 414 and on the upstream side of the heating side compressor 411, such that the heating side coolant can flow therethrough; and an injection valve 422 capable of adjusting a flow rate of the coolant flowing through the injection flow path 421. In the injection circuit 420, by adjusting an opening degree of the injection valve 422, the condensed heating side coolant flowing on the downstream side of the heating side condenser 412 can be bypassed to the upstream side of the heating side compressor 411.

The hot gas circuit 424 includes: a hot gas flow path 425, which communicates (connects) a part of the heating side refrigerating circuit 410, which is located on the downstream side of the heating side compressor 411 and on the upstream side of the heating side condenser 412, and a part of the injection flow path 421, which is located on the downstream side of the injection valve 422, such that the coolant can flow therethrough; and a hot gas valve 426 capable of adjusting a flow rate of the coolant flowing through the hot gas flow path 425. By opening an opening degree of the hot gas valve 426, the hot gas circuit 424 can bypass the coolant having a high temperature and high pressure, which flows on the downstream side of the heating side compressor 411, to the upstream side of the heating side compressor 411.

In addition, in this embodiment, the supercooling circuit 416 includes: a supercooling bypass flow path 417, which communicates (connects) a part of the heating side refrigerating circuit 410, which is located on the downstream side of the heating side condenser 412 and on the upstream side of a positon connected to the injection flow path 421, and the heating side compressor 411 in the heating side refrigerating circuit 410, such that the heating side coolant can flow therethrough; and a supercooling control valve 418 which controls a flow rate of a coolant flowing through the supercooling bypass flow path 417. In this embodiment, a part of the supercooling bypass flow path 417, which is located on the downstream side of the supercooling control valve 418, and a part of the heating side refrigerating circuit 410, which is located on the downstream side of a position connected to the supercooling bypass flow path 417 and on the upstream side of the position connected to the injection flow path 421 constitute a supercooling heat exchanger SC where they can be heat-exchanged with each other.

In the supercooling heat exchanger SC, by opening the supercooling control valve 418, the condensed heating side coolant flowing on the downstream side of the heating side condenser 412 is expanded on the downstream side of the supercooling control valve 418 in the supercooling bypass flow path 417 to have a low temperature, so that a super cooling degree can be given to the coolant that flows from the heating side condenser 412 toward the heating side expansion valve 413 through the supercooling heat exchanger SC. On the other hand, the heating side coolant having flown through the supercooling bypass flow path 417 flows into a part of the heating side refrigerating circuit 410, which is located on the upstream side of the heating side compressor 411 and on the downstream side of the heating side evaporator 414. Specifically in this embodiment, during the compression of the heating side coolant by the heating side compressor 411, the coolant having flown through the supercooling bypass flow path 417 is configured to merge with a heating side coolant having passed through the heating side evaporator 414, which is being compressed in the heating side compressor 411.

In the illustrated example, a receiver tank 415A and a filter dryer 415B are disposed in this order at a position of the heating side refrigerating circuit 410, which is located on the downstream side of the heating side condenser 412 and on the upstream side of the position connected to the supercooling bypass flow path 417.

Returning to FIG. 4, the heating side brine circulation apparatus 403 includes: a heating side brine circulation path 431 having an loop-like shape in order for circulating a heating side brine; a heating unit side main heating part 432 constituting a part of the heating side brine circulation path 431 and capable of heating the heating side brine received therein; a heating side pump 433 constituting a part of the heating side brine circulation path 431 and giving a driving force for circulating the brine in the heating side brine circulation path 431; a first heating unit side sub heating part 434A and a second heating unit side sub heating part 434B which are located on the downstream side of the heating side pump 433 to constitute a part of the heating side brine circulation path 431, and are capable of heating the heating side brine received therein; a first loading part 435A located on the downstream side of the first heating unit side sub heating part 434A to constitute a part of the heating side brine circulation path 431; a second loading part 435B located on the downstream side of the second heating unit side sub heating part 434B to constitute a part of the heating side brine circulation path 431; and a heating side brine tank 436 connected to the heating unit side main heating part 432. The heating side brine is a substance that can release or absorb the heat in the loading parts 435A and 435B without changing phase or insofar as it does not change phase, and a kind thereof is selected depending on a desired temperature control range. The heating side brine may be an ethylene glycol solution, a calcium chloride solution or water, for example.

In this embodiment, a part of the heating side brine circulation path 431, which is on the downstream side of the heating side pump 433, is branched to a first branch part 431A and a second branch part 431B. The first heating unit side sub heating part 434A and the first loading part 435A respectively constitute a part of the first branch part 431A, and the second heating unit side sub heating part 434B and the second loading part 435B respectively constitute a part of the second branch part 431B. The first branch part 431A and the second branch part 431B merge with each other on the downstream side of the first loading part 435A and the second loading part 435B. The brine having passed through the merged position of the first branch part 431A and the second branch part 431B passes through the below-described heating capacity adjusting heat exchanger HC, and then flows toward the heating unit side main heating part 432. After the brine has passed through the heating unit side main heating unit 432, the brine again flows into the first branch part 431A and the second branch part 431B.

When the heating side brine is driven by the heating side pump 433 to circulate in the heating side brine circulation path 431, each of the heating unit side main heating part 432, the first heating unit side sub heating part 434A and the second heating unit side sub heating part 434B can heat the heating-side brine, which is received along with the circulation of the heating side brine, at a desired heating amount. Each of the heating parts 432, 434A and 434B has a case part into which a heating side brine flows and a heater disposed in the case part, and is capable of adjusting a heating capacity of the heating side brine by adjusting a heating amount of the heater. In the illustrated example, the first heating unit side main heating part 432 is equipped with a plurality of heaters, and each of the first heating unit side sub heating part 434A and the second heating unit side sub heating part 434B is equipped with one heater. However, the number of heaters is not particularly limited, and may be selected depending on a highest control temperature set in the temperature control space S.

As shown in FIG. 4, in this embodiment, the first loading part 435A and the second loading part 435B are disposed in the chamber 10, so that they can cause the heat of the brine to be released to the temperature control space S, or can cause the heat of the temperature control space S to be absorbed by the brine. Namely, when the temperature control space S is heated, the heating unit 60 causes the heat of the first loading part 435A and the second loading part 435B to be released therefrom to the temperature control space S, and when the temperature control space S is cooled, the heating unit 60 causes the heat of the temperature control space S to be absorbed in the first loading part 435A and the second loading part 435B.

In addition, the brine is stored in the heating side brine tank 436. The air layer part is formed between the liquid level of the stored brine and the upper wall of the heating side brine tank 436. The case part of the heating unit side main heating part 432 is in fluid connection to the air layer part and the liquid layer part of the heating side brine in the heating side brine tank 436.

In this embodiment, as shown in FIG. 4, a part of the heating side brine circulation path 431 and the heating side evaporator 414 of the heating side refrigerating apparatus constitute the heating capacity adjusting heat exchanger HC where they can be heat-exchanged with each other. In more detail, in this embodiment, a part of the heating side brine circulation path 431, which is located on the downstream side of the first loading part 435A and the second loading part 435B and on the upstream side of the heating unit side main heating part 432, and the heating side evaporator 414 constitute the heating capacity adjusting heat exchanger HC. Thus, the heating side brine in the heating side brine circulation apparatus 403 can be cooled by the heating side refrigerating apparatus 402. In this embodiment, the heating side brine cooled by the heating side refrigerating apparatus 402 is heated by the heating unit side main heating part 432, the first heating unit side sub heating part 434A and the second heating unit side sub heating part 434B, or passes them without being heated, whereby a temperature of the temperature control space S can be controlled at a desired heating capacity or refrigerating capacity.

<Control Apparatus>

Next, the control apparatus 70 is described. FIG. 4 shows the control apparatus 70, and a plurality of temperature sensors and pressure sensors disposed on the cooling unit 50 and the heating unit 60. In this embodiment, based on the detection of the temperature sensors and the pressure sensors, the control apparatus 70 is configured to control the respective parts of the cooling unit 50 (low temperature side pump 333, first low temperature side compressor 311, second low temperature side compressor 321, low temperature side heating part 332 and the like), and the respective parts of the heating unit 60 (heating side pump 433, heating side compressor 411, injection valve 422, hot gas valve 426, heating units 432, 434A and 434B and the like).

For example, the control apparatus 70 in this embodiment can switch driving and stopping of the low temperature side pump 333, the first low temperature side compressor 311 and the second low temperature side compressor 321, and can switch driving and stopping of the heating side pump 433 and the heating side compressor 411. In addition, the control apparatus 70 adjusts an opening degree of the injection valve 422 and an opening degree of the hot gas valve 426 based on a set target refrigerating capacity so as to to adjust a flow rate of the heating side coolant flowing into the heating side evaporator 414, such that the heating side evaporator 414 can output the target refrigerating capacity. The target refrigerating capacity may be calculated by the control apparatus 70, depending on a target temperature set by a user in the temperature control space S.

In FIG. 5, the reference number 428 depicts a temperature sensor that detects a temperature of the heating side coolant from the downstream side of the heating side evaporator 414 before it flows into the heating side compressor 411, and the reference number 429 depicts a pressure sensor that detects a pressure of the heating side coolant from the downstream side of the heating side evaporator 414 before it flows into the heating side compressor 411. In the illustrated example, the heating side temperature sensor 428 and the heating side pressure sensor 429 are located on the downstream side of a position at which the injection circuit 420 and the hot gas circuit 424 are connected to the heating side refrigerating circuit 410. In this embodiment, when a refrigerating capacity of the heating side refrigerating apparatus 402 is adjusted, the control apparatus 70 adjusts an opening degree of the injection valve 422 and an opening degree of the hot gas valve 426 based on a temperature detected by the temperature sensor 428 and a pressure detected by the pressure sensor 429. Thus, the heating side coolant flowing into the heating side compressor 411 is allowed to be in a gas phase and to have a predetermined temperature or less. The predetermined temperature is about a temperature by which the heating side compressor 411 is not burned.

<Structure in Chamber 10>

Figure 10:
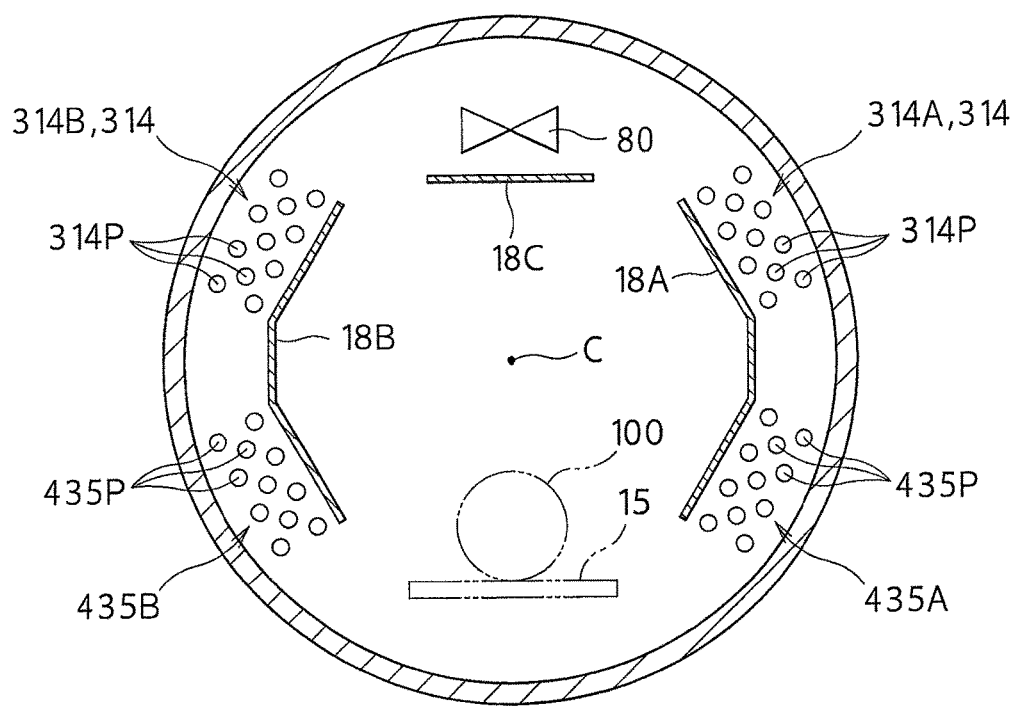
FIG. 10 is a longitudinal (vertical) sectional view of a chamber of the environmental testing apparatus shown in FIG. 4.

FIG. 10 shows a longitudinal (vertical) section of the chamber 10 of the environmental testing apparatus 2 shown in FIG. 4. As shown in FIG. 10, the first low temperature side evaporator 314 in this embodiment includes a first evaporator 314A located on one horizontal side in the chamber, and a second evaporator 314B located on the other horizontal side in the chamber 10. The first evaporator 314A and the second evaporator 314B are respectively supplied with the first low temperature side coolant decompressed by the first low temperature side expansion valve 313. The first low temperature side coolants having passed through the first evaporator 314A and the second evaporator 314B merge with each other, and then flow toward the first low temperature side compressor 311.

Here, each of the first evaporator 314A and the second evaporator 314B includes a plurality of pipe parts 314P each of which extends in the same direction (in this embodiment, in the direction of the central axis C). In the respective first evaporator 314A and the second evaporator 314B, when seen in a section perpendicular to an extension direction of the pipe part 314P, the plurality of pipe parts 314P are disposed in a staggered arrangement. The first low temperature side coolant flows through each of these pipe parts 314P.

In addition, the first loading part 435A of the heating unit 60 is located on one horizontal side in the chamber 10, and the second loading part 435B thereof is located on the other horizontal side in the chamber 10. Each of the first loading part 435A and the second loading part 435B also includes a plurality of pipe parts 435P each of which extends in the same direction (in this embodiment, in the direction of the central axis C). In the respective first loading part 435A and the second loading part 435B, when seen in a section perpendicular to an extension direction of the pipe part 435P, the plurality of pipe parts 435P are disposed in a staggered arrangement.

An installation space for an object to be tested is formed between the first evaporator 314A and the first loading part 435A, and the second evaporator 314B and the second loading part 435B. In this embodiment, the first evaporator 314A is located above the first loading part 435A, and the second evaporator 314B is located above the second loading part 435B. A first cover 18A, which covers the first evaporator 314A and the first loading part 435A, is disposed between the first evaporator 314A and the first loading part 435A, and the installation space. Namely, the first cover member 18A is close to the first evaporator 314A and the first loading part 435A, and covers the first evaporator 314A and the second loading part 435A from the installation space side. In addition, a second cover member 18B, which covers the second evaporator 314B and the second loading part 435B, is disposed between the second evaporator 314A and the second loading part 435B, and the installation space. Namely, the second cover member 18B is close to the second evaporator 314B and the second loading part 435B, and covers the second evaporator 314B and the second loading part 435B from the installation space side. Further, a fan 80 is located above the installation space in the chamber 10. A third cover member 18C, which covers the fan 80 from the installation space side, is located in the chamber 10. The fan 80 is configured to blow air toward the third cover member 18C.

<Operation>

Next, an operation of the environmental testing device 2 according to this embodiment is described with reference to FIGS. 6 to 8. The environmental testing apparatus 2 is configured to adjust a temperature of the temperature control space S to a desired temperature in a low temperature zone, a mid temperature zone or a high temperature zone, by the control of the control apparatus 70 which switches operation states of the cooling unit 50 and the heating unit 60. In this embodiment, for example, the low temperature zone is a range of between −60° C. and −20° C., the mid temperature zone is a range of between −19° C. and +25° C., and the high temperature zone is a range of between +26° C. and +120° C. However, these respective ranges are not particularly limited.

Figure 6:
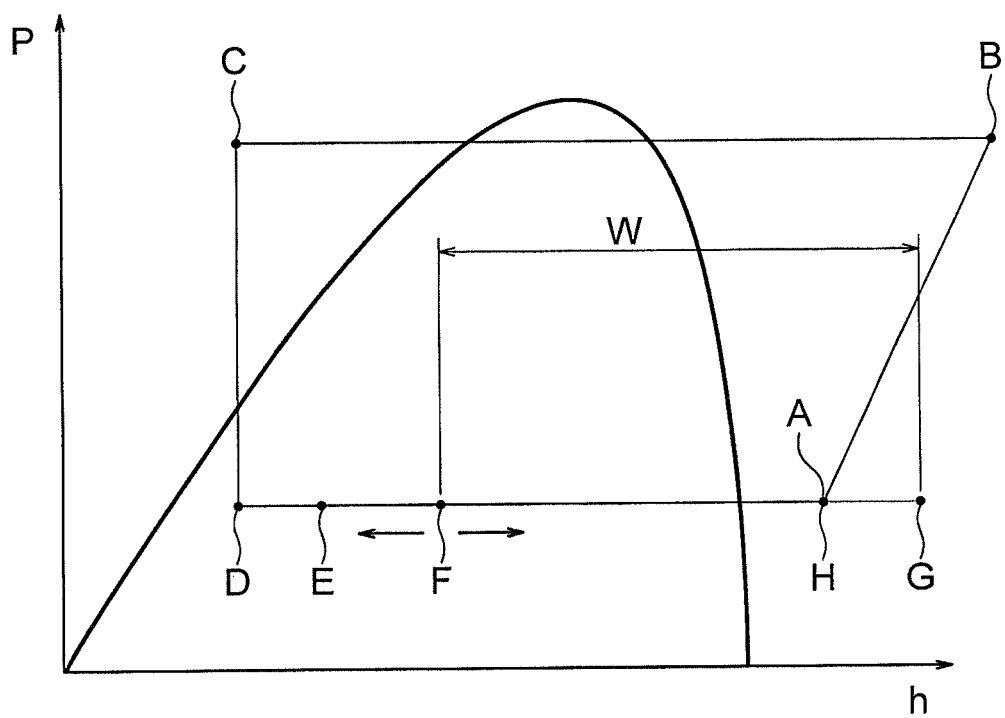
FIG. 6 is a view showing an example of a Mollier diagram (P-h diagram) of a low temperature side refrigerating apparatus in a cooling unit of the environmental testing apparatus shown in FIG. 4.
Figure 7:
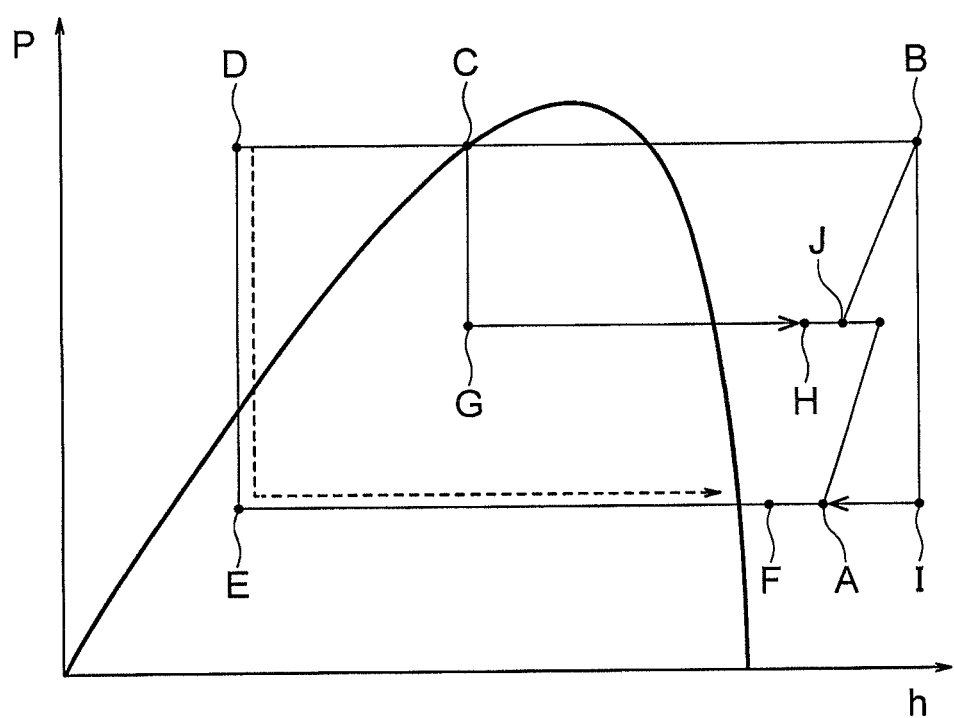
FIG. 7 is a view showing an example of a Mollier diagram of the heating side refrigerating apparatus in the heating unit of the environmental testing apparatus shown in FIG. 4.
Figure 8:
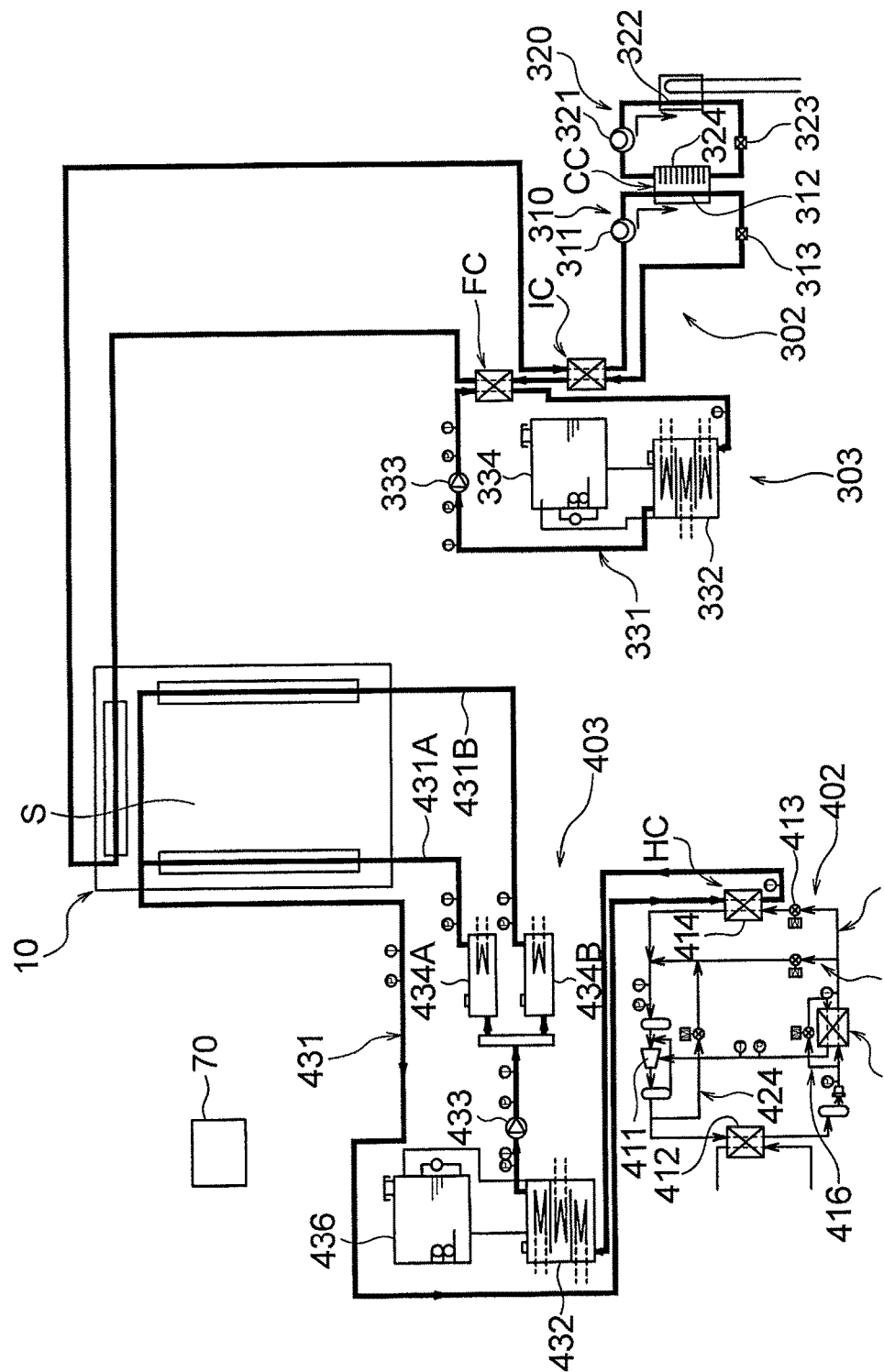
FIG. 8 is a view showing a condition where a temperature control in a low temperature zone is performed in the environmental testing apparatus shown in FIG. 4.
Figure 9:
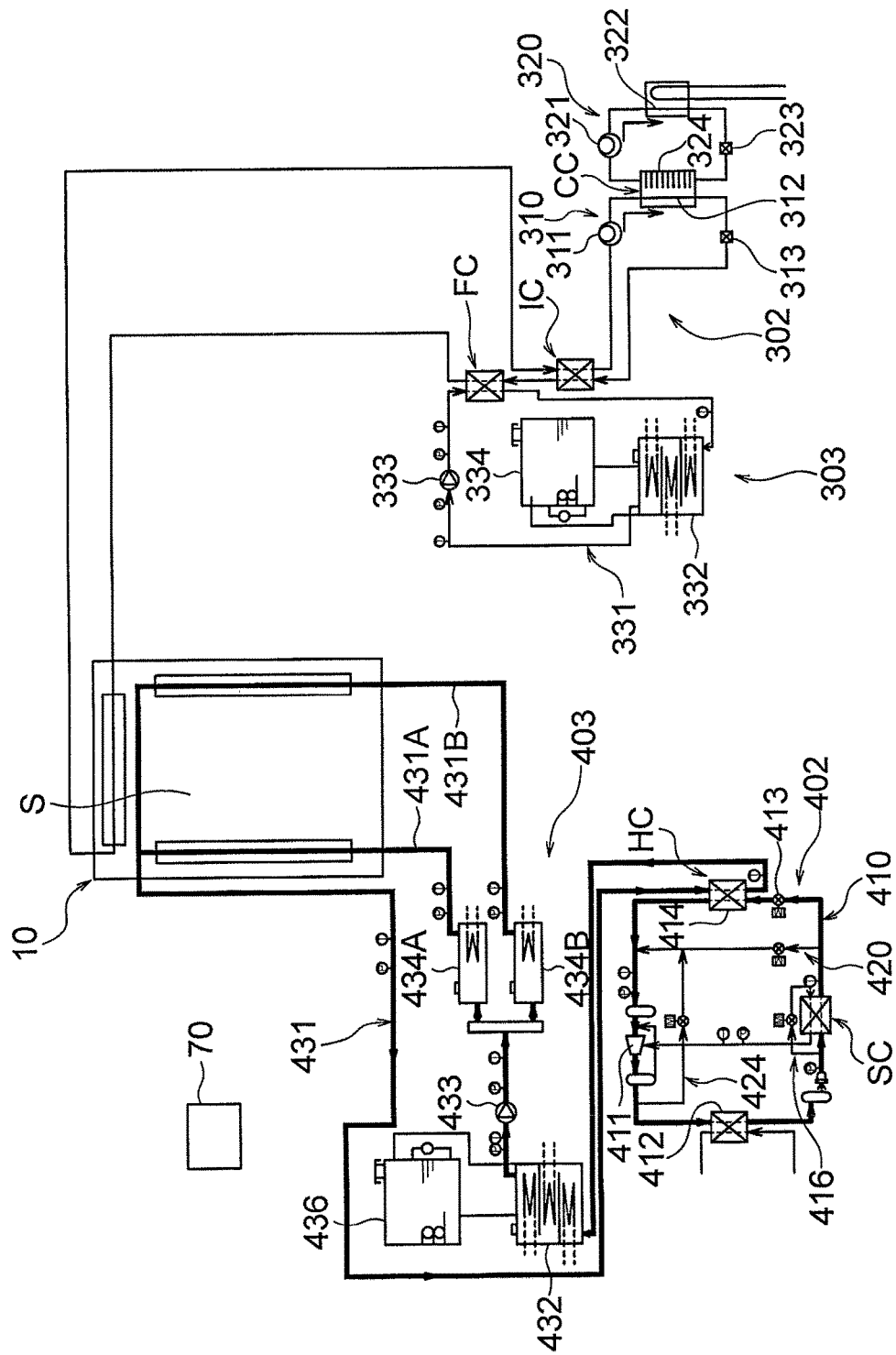
FIG. 9 is a view showing condition where a temperature control in a mid temperature zone or high temperature zone is performed in the environmental testing apparatus shown in FIG. 4.

FIG. 6 is a view showing an example of a Mollier diagram of the first low temperature side refrigerating circuit 310 in the cooling unit 50, and FIG. 7 is a view showing an example of a Mollier diagram of the heating side refrigerating apparatus 402 in the heating unit 60. FIG. 8 shows a view showing a condition where a temperature control in the low temperature zone is performed, and FIG. 9 shows a view showing a condition where a temperature control in the mid temperature zone or the high temperature zone is performed. Herebelow, control manners in the low temperature zone, the mid temperature zone and the high temperature zone are described in this order.

(Temperature Control in Low Temperature Zone)

When a temperature control in the low temperature zone is performed, in the cooling unit 50, the first low temperature side compressor 311, the second low temperature side compressor 321 and the low temperature side pump 333 are driven. On the other hand, in the heating unit 60, the heating side pump 433 is driven in the heating side brine circulation apparatus 403, and the heating side refrigerating apparatus 402 is stopped, whereby the heating side coolant is not circulated. In FIG. 8, the bold lines described on the pipes show lines through which a coolant or brine is circulated to illustrate an operation condition upon the temperature control in the low temperature zone.

At this time, in the first low temperature side refrigerating circuit 310, the first low temperature side coolant compressed by the first low temperature side compressor 311 flows into the first low temperature side condenser 312 constituting the cascade condenser CC, and is condensed by the second low temperature side evaporator 324 of the second low temperature side refrigerating circuit 320. Thereafter, the first low temperature side coolant is decompressed by the first low temperature side expansion valve 313 to have a low temperature, and flows into the first low temperature side evaporator 314. The first low temperature side coolant having flown into the first low temperature side evaporator 314 absorbs the heat in the temperature control space S, and flows into the first low temperature side compressor 311.

In this embodiment, due to the provision of the internal heat exchanger IC, the first low temperature side coolant having passed through the fist low temperature side evaporator 314 to have an elevated temperature is cooled by the first low temperature side coolant of a low temperature ejected by the first low temperature side expansion valve 313, before the first low temperature side coolant is sucked into the first low temperature side compressor 311. Thus, it can be restrained that the first low temperature side coolant having an excessive superheating degree is sucked into the first low temperature side compressor 311.

On the other hand, in the second low temperature side refrigerating circuit 320, a second low temperature side coolant having absorbed the heat of the first low temperature side coolant in the cascade condenser CC is compressed by the second low temperature side compressor 321. The compressed second low temperature side coolant flows into the second low temperature side compressor 322 so as to be condensed by cooling water flowing in the second low temperature side condenser 322. Thereafter, the second low temperature side coolant is decompressed by the second low temperature side expansion valve 323 to have a low temperature, and flows into the second low temperature side evaporator 324 constituting the cascade condenser CC so as to again cool the first coolant having flown into the first low temperature side condenser 312. In this embodiment, the first low temperature side compressor 311 and the second low temperature side compressor 321 are driven at a constant pressure for the purpose of control safety.

In the low temperature side brine circulation apparatus 303, a low temperature side brine is circulated in the low temperature side brine circulation path 331, so that the low temperature side brine can be suitably heated by the low temperature side heating part 332.

In this embodiment, since the refrigerating capacity adjusting mechanism FC is provided, the first low temperature side coolant can be heated by the brine heated by the low temperature side heating apt 332, at a part of the first low temperature side refrigerating circuit 310 of the low temperature side refrigerating apparatus 302, which is on the upstream side of the first low temperature side evaporator 314. At this time, a refrigerating capacity of the first low temperature side evaporator 314 can be adjusted depending on a heating capacity of the brine.

On the other hand, in the heating side brine circulation apparatus 403, a heating side brine is circulated in the heating side brine circulation path 431, so that the heating side brine can be suitably heated by the heating unit side main heating unit 432 and so on. In the temperature control in the low temperature zone performed by the cooling unit 50, when the temperature control in the low temperature zone is switched to the temperature control in the mid temperature zone or the high temperature zone, the structure that circulates the heating side brine makes it possible to effectively reduce a time required for a temperature in the low temperature zone to reach a desired temperature in the mid temperature zone or the high temperature zone. When the temperature control in the low temperature zone is performed, the heating side brine is not heated.

A refrigerating capacity adjustment performed in the cooling unit 50 is described in detail with reference to FIG. 6. As shown in FIG. 6, in a refrigeration cycle in the cooling unit 50, as shown by the transition from the point A to the point B, the first low temperature side coolant sucked into the first low temperature side compressor 311 is compressed. The first low temperature side coolant ejected by the first low temperature side compressor 311 is condensed by the first low temperature side condenser 312 so as to be cooled, whereby its specific enthalpy decreases, as shown by the transition from the point B to the point C.

Then, as shown by the transition from the point C to the point D, the first low temperature side coolant condensed by the first lower temperature side condenser 312 is decompressed by the first low temperature side expansion valve 313 to have a low temperature. Thereafter, the first low temperature side coolant ejected from the first low temperature side expansion valve 313 is heat-exchanged, in the internal heat exchanger IC, with the first low temperature side coolant immediately before it flows into the first low temperature side compressor 311, so as to absorb the heat whereby its specific enthalpy increases, as shown by the transition from the point D to the point E. Thereafter, the first low temperature side coolant is heat-exchanged with the heated low temperature side brine in the refrigerating capacity adjusting mechanism FC, so as to absorb the heat whereby its specific enthalpy increases, as shown by the transition from the point E to the point F.

Following thereto, the first low temperature side coolant flows into the first low temperature side evaporator 314 and absorbs the heat of the temperature control space S, whereby its specific enthalpy increases, as shown by the transition from the point F to the point G. Then, the first low temperature side coolant having passed through the first low temperature side evaporator 314 is heat-exchanged, in the internal heat exchanger IC, with the low-temperature first low temperature side coolant ejected from the first low temperature side expansion valve 313, so as to be cooled whereby its specific enthalpy decreases, as shown by the transition shown by the point G to the point H. Thus, it can be restrained so that the first low temperature side coolant having an excessive superheating degree is sucked into the first low temperature side compressor 311. After that, the first low temperature side coolant flows into the first low temperature side compressor 311 so as to be compressed.

In the aforementioned Mollier diagram, the position of the point F can be varied as shown by the arrows, depending on a heating capacity of the heated low temperature side brine. A refrigerating capacity of the first low temperature side refrigerating circuit 310 is in proportion to a difference, which is shown by the symbol W, between the specific enthalpy of the first low temperature side coolant immediately before it flows into the first low temperature side evaporator 314 and the specific enthalpy of the first low temperature side coolant immediately after it flows out from the first low temperature side evaporator 314. Thus, in this embodiment, by adjusting a heating capacity of the heated low temperature side brine, a refrigerating capacity of the first low temperature side refrigerating circuit 310 can be adjusted.

(Temperature Control in Mid Temperature Zone)

When a temperature control in the mid temperature zone is performed, in the cooling unit 50, the first low temperature side compressor 311, the second low temperature side compressor 321 and the low temperature side pump 333 are not driven. On the other hand, in the heating unit 60, the heating side pump 433 of the heating side brine circulation apparatus 403 is driven, and the heating side compressor 411 of the heating side refrigerating apparatus 402 is driven. In FIG. 9, the bold lines described on the pipes show lines through which a coolant or brine is circulated to illustrate an operation condition upon the temperature control in the mid temperature zone.

At this time, in the heating side refrigerating circuit 410 of the heating side refrigerating apparatus 402, the heating side coolant compressed by the heating side compressor 411 flows into the heating side condenser 412 so as to be condensed. Thereafter, the heating side coolant passes through the supercooling heat exchanger SC. At this time, when the supercooling control valve 418 is opened, the condensed heating side coolant flowing on the downstream side of the heating side condenser 412 is expanded in the supercooling bypass flow path 417 on the downstream side of the supercooling control valve 418 to have a low temperature, whereby a supercooling degree can be given to the heating side coolant flowing from the heating side condenser 412 toward the heating side expansion valve 413 through the supercooling heat exchanger SC. The coolant expanded by the supercooling control valve 418 flows into the heating side compressor 411, with the heat being absorbed in the coolant.

Thereafter, the heating side coolant passing through the heating side expansion valve 413 is decompressed to have a low temperature, and flows into the heating side evaporator 414. The coolant having flown into the heating side evaporator 414 can be heat-exchanged with the heating brine in the heating capacity adjusting heat exchanger HC. When the heating side brine has a temperature higher than that of the heating side coolant, the heating side coolant absorbs the heat and flows into the heating side compressor 411.

In this embodiment, owing to the provision of the injection circuit 420 and the hot gas circuit 424, the heating side coolant condensed by the heating side condenser 412 can be passed through the injection circuit 420 without allowing it to flow into the heating side evaporator 414, so as to be bypassed to the downstream side of the heating side evaporator 414, and the high-temperature heating side coolant ejected by the heating side compressor 411 can be passed through the hot gas circuit 424 so as to be bypassed to the downstream side of the heating side evaporator 414. Thus, a flow rate of the heating side coolant flowing into the heating side evaporator 414 can be controlled, whereby a refrigerating capacity outputted by the heating side evaporator 414 can be flexibly adjusted.

At this time, in this embodiment, the control apparatus 70 adjusts a flow rate of the coolant flowing into the heating side evaporator 414 by adjusting an opening degree of the injection valve 422 and an opening degree of the hot gas valve 426 based on a set target refrigerating capacity, such that the heating side evaporator 414 can output the target refrigerating capacity. At this time, the control apparatus 70 adjusts an opening degree of the injection valve 422 and an opening degree of the hot gas valve 426 based on a temperature detected by the temperature sensor 428 and on a pressure detected by the pressure sensor 429, whereby the coolant flowing into the heating side compressor 411 is allowed to be in a gas phase and to have a predetermined temperature or less.

In order to obtain the aforementioned target refrigerating capacity, a flow rate of the heating side coolant flowing through the heating side evaporator 414 is adjusted. To this end, an amount of the heating side coolant to be bypassed may be optionally assigned to the injection circuit 420 and the hot gas circuit 424. Thus, it is easy to allow the coolant flowing into the heating side compressor 411 to be in a gas phase and to have a predetermined temperature or less. In addition, in this embodiment, since the heating side coolant from the hot gas circuit 424 is configured to flow into the injection flow path 421 before it reaches the heating side refrigerating circuit 410, the heating side coolant can be restrained from having an excessively high temperature in the heating side refrigerating circuit 410 and the heating side compressor 411. Thus, burning of the heating side compressor 411 and the like can be restrained.

FIG. 7 shows a Mollier diagram of the heating side refrigerating apparatus 402 in the heating unit 60, wherein the injection circuit 420 and the hot gas circuit 424 are operated, and the supercooling circuit 416 is operated, so that the heating side brine is cooled. As shown in FIG. 7, in a refrigerating cycle in the heating unit 60, the heating side coolant sucked into the heating side compressor 411 is compressed, as shown by the transition from the point A to the point B. The coolant ejected by the heating side compressor 411 is condensed by the heating side condenser 412 so as to be cooled, whereby its enthalpy decreases, as shown by the transition from the point B to the point C.

Then, a supercooling degree is given to, in the supercooling heat exchanger SC, a part of the heating side coolant condensed by the heating side condenser 412 whereby its specific enthalpy decreases, as shown by the transition shown by the point C to the point D. On the other hand, the coolant flowing through the supercooling bypass flow path 417 in the supercooling heat exchanger SC, which gives a supercooling degree, is expanded by the supercooling control valve 418 so as to be decompressed down to a middle pressure, for example, as shown by the transition shown by the point C to the point G. Thereafter, the coolant is heat-exchanged in the supercooling heat exchanger SC, so as to absorb the heat whereby its enthalpy increases, as shown by the transition from the point G to the point H.

The coolant to which the supercooling degree has been given in the supercooling heat exchanger SC is decompressed by the heating side expansion valve 413 to have a low temperature, as shown by the transition from the point D to the point E. Thereafter, the heating side coolant ejected from the heating side expansion valve 413 is heat-exchanged with the heating side brine in the heating side evaporator 414, i.e., the heating capacity adjusting heat exchanger HC, so as to absorb the heat whereby its enthalpy increases, as shown by the transition from the point E to the point F. A flow rate of the coolant passing through the heating side evaporator 414 is controlled to adjust a refrigerating capacity thereof, by the control apparatus 70 which controls the respective valves of the injection circuit 420 and the hot gas circuit 424 to generate a heating side coolant that does not pass through the heating side evaporator 414.

In FIG. 7, as shown from the point B to the point I, the heating side coolant, which is bypassed to the upstream side of the heating side compressor 411 through the hot gas circuit 424, is decompressed by the hot gas valve 426. In addition, as shown by the dashed line extending from the point D, the heating side coolant, which is bypassed to the upstream side of the heating side compressor 411 through the injection circuit 420, is decompressed by the injection valve 422. On the upstream side of the heating side compressor 411, the heating side coolant having passed through the heating side evaporator 414, which is in the condition shown by the point F, the heating side coolant having been bypassed through the hot gas circuit 424, and the heating side coolant having been bypassed though the injection circuit 420 are mixed (point A). Since the position of the point A can be adjusted by the control apparatus 70 which adjusts a ratio between the heating side coolant bypassed through the hot gas circuit 424 and the heating side coolant bypassed through the injection circuit 420, it is easy to allow the heating side coolant flowing into the heating side compressor 411 to be in a gas phase and to have a predetermined temperature or less. Thereafter, the heating side coolant is composed by the heating side compressor 411 so as to be moved from the point A to the high pressure side. In the course of this movement, the heating side coolant is mixed with the heating side coolant form the supercooling bypass flow path 417, and reaches the point J. Thereafter, the coolant is compressed to the point B.

On the other hand, in the heating side brine circulation apparatus 403, the heating side brine is circulated in the heating side brine circulation path 431, so that the heating side brine can be suitably heated by the heating unit side main heating part 432, the first heating unit side sub heating part 434A and the second heating unit side sub heating part 434B. In this embodiment, the part of the heating side brine circulation path 431, which is located on the downstream side of the first loading part 435A and the second loading part 435B and on the upstream side of the heating unit side main heating part 432, and the heating side evaporator 414 constitute the heating capacity adjusting heat exchanger HC. Thus, the heating side brine in the heating side brine circulation apparatus 403 can be cooled by the heating side refrigerating apparatus 402. In this embodiment, the heating side brine cooled by the heating side refrigerating apparatus 402 is heated by the heating unit side main heating part 432, the first heating unit side sub heating part 434A and the second heating unit side sub heating part 434B, or passes them without being heated, whereby a temperature of the temperature control space S can be controlled at a desired heating capacity or refrigerating capacity.

(Temperature Control in High Temperature Zone)

When a temperature control in the high temperature zone is performed, similarly to the case of the mid temperature zone, in the cooling unit 50, the first low temperature side compressor 311, the second low temperature side compressor 321 and the low temperature side pump 333 are not driven. On the other hand, in the heating unit 60, the heating side pump 433 of the heating side brine circulation apparatus 403 is driven, and the heating side compressor 411 of the heating side refrigerating apparatus 403 is driven. However, a flow rate of the heating side brine to be circulated in the heating side brine circulation apparatus 402 is made larger than a flow rate in the case of the mid temperature zone. When the temperature control in the high temperature zone is performed, a flow rate of the heating side brine to be circulated may be about 1.5 to 3 times a flow rate in the case of the mid temperature zone, for example.

As described above, according to the environmental testing apparatus 2 according to this embodiment, in the cooling unit 50, the first low temperature side coolant can be heated by the low temperature side brine at a part of the first low temperature side refrigerating circuit 310 of the low temperature side refrigerating apparatus 302, which is located on the upstream side of the first low temperature side evaporator 314. At this time, a refrigerating capacity of the first low temperature side evaporator 314 can be adjusted depending on a heating capacity of the low temperature side brine. Thus, a refrigerating capacity of the first low temperature side refrigerating circuit 310 can be widely adjusted in a simple manner, without operating any constituent element of the refrigerating circuit 310. In addition, in the heating unit 60, the heating side coolant condensed by the heating side condenser 412 can be passed through the injection circuit 420 without allowing it to flow into the heating side evaporator 414, so as to be bypassed to the downstream side of the heating side evaporator 414, as well as the high-temperature heating side coolant ejected by the heating side compressor 411 can be passed through the hot gas circuit 424 so as to be bypassed to the downstream side of the heating side evaporator 414. Thus, a flow rate of the heating side coolant flowing into the heating side evaporator 414 can be controlled, whereby a refrigerating capacity outputted by the heating side evaporator 414 can be flexibly adjusted. At this time, since the heating side coolant flowing into the heating side evaporator 414 is not mixed with the high-pressure heating side coolant, the refrigerating capacity to be outputted can be made stable. In addition, by adjusting a ratio between the condensed heating side coolant bypassed through the injection circuit 420 and the high-temperature heating side coolant bypassed through the hot gas circuit 424, the condition and temperature of the heating side coolant to flow into the heating side compressor 411 can be easily controlled desirably. Thus, the stable temperature control can be performed while flexibly adjusting the refrigerating capacity. Thus, since a temperature of the heating side brine of the heating side brine circulation apparatus 403 can be controlled such that a heating capacity or a refrigerating capacity of the loading parts 435A and 435B can be adjusted by the stably adjusted refrigerating capacity outputted by the heating side refrigerating apparatus 402, the stable temperature control can be achieved by means of the loading parts 435A and 435B. Since the cooling unit 50 and the heating unit 60 have the different temperature control ranges, a sufficiently broad temperature control range from a low temperature to a high temperature can be ensured.

As a result, a sufficiently broad temperature control range from a low temperature to a high temperature can be ensured, whereby a temperature of a space whose temperature to be controlled or an object whose temperature to be controlled can be stably controlled within a desired temperature control range in an easy manner.

In addition, in this embodiment, in a temperature control to a desired temperature in the low temperature zone by circulating the first low temperature side coolant by the low temperature side refrigerating apparatus 302 and by circulating the low temperature side brine by the low temperature side brine circulation apparatus 303, when the temperature control in the low temperature zone is switched to a temperature control in the mid temperature zone or in the high temperature zone by circulating the heating side brine by the heating side brine circulation apparatus 403, since the temperature control by the heating side brine can be rapidly performed, a time required for the temperature in the low temperature zone to reach a desired temperature in the mid temperature zone or in the high temperature zone can be effectively reduced. In addition, when a temperature control in the mid temperature zone is switched to a temperature control in the high temperature zone, by making larger a flow rate of the heating side brine circulated by the heating side brine circulation apparatus 403 than the flow rate in the case of the temperature control in the mid temperature zone, a time required for the temperature in the mid temperature zone to reach a required temperature in the high temperature zone can be effectively reduced.

In addition, in this embodiment, the low temperature side coolant having passed through the first low temperature side evaporator 314 to have an elevated temperature is cooled, before it is sucked into the low temperature side compressor 311, by the low-temperature first low temperature side coolant ejected by the first low temperature side expansion valve 313. Thus, the low temperature side coolant having an excessive superheating degree can be restrained from being sucked into the first low temperature side compressor 311. Thus, thermal decomposition of the first low temperature side coolant and burning of the first low temperature side compressor 311 can be restrained, whereby stability in temperature control can be improved. Particularly when the cooling by the cooling unit 50 is performed after the heating by the heating unit 60 has been performed, it increases the risk in which the first low temperature side coolant, which has been heat-exchanged by the first low temperature side evaporator 314 in the cooling unit 50, has an excessive superheating degree. However, it can be restrained that such a first low temperature side coolant is sucked into the first low temperature side compressor 311. Thus, suitable temperature control stability in the system using both the cooling unit 50 and the heating unit 60 can be ensured.

In addition, in this embodiment, since a refrigerating capacity of the heating side coolant can be increased by the supercooling heat exchanger SC, an adjustment range of the refrigerating capacity can be enlarged. In addition, since the heating side coolant ejected from the supercooling heat exchanger SC is bypassed through the injection circuit 420, it is possible to effectively decrease a temperature of the high-temperature heating side coolant that is bypassed to the downstream side of the heating side evaporator 414 through the hot gas circuit 424. In particular, when the heating of the heating unit 60 is performed after the cooling by the cooling unit 50 has been performed, if there is not provided the supercooling heat exchanger SC, the heating side coolant, which is heat-exchanged with the heating side brine in the heating side evaporator 414 in the heating unit 60, cannot sufficiently ensure a superheating degree, which may increase a risk of lowering a refrigerating capacity. However, the the supercooling heat exchanger SC can compensate a refrigerating capacity. Thus, undesired lowering of a refrigerating capacity in the heating side evaporator 414 can be restrained, whereby suitable temperature control stability in the system using both the cooling unit 50 and the heating unit 60 can be ensured.

In addition, since the low temperature side refrigerating apparatus 302 is a binary refrigerating apparatus, a high refrigerating capacity in the low temperature side refrigerating apparatus 302 can be ensured as compared with a case in which the low temperature side refrigerating apparatus 302 is of a unitary type, as well as an adjustable refrigerating capacity range can be widened to enlarge a controllable temperature zone.

What is claimed is:

1. An environmental testing apparatus comprising:
a chamber that accommodates an object to be tested;
a cooling unit including: a brine circulation apparatus that has a brine circulation path a part of which is located in the chamber, and circulates a brine in the brine circulation path; and a cooling apparatus that cools the brine in a part of the brine circulation path, which is located outside the chamber;
a heating unit including a heater located in the chamber; and
a control apparatus that controls the cooling unit and the heating unit;
wherein:
the cooling apparatus includes: a high temperature side cooling circuit in which a high temperature side compressor, a condenser, a high temperature side expansion valve and a cascade condenser are connected in this order by pipes so as to circulate a high temperature side heat medium; and a low temperature side cooling circuit in which a low temperature side compressor, the cascade condenser, a low temperature side expansion valve and an evaporator are connected in this order by pipes so as to circulate a low temperature side heating medium; with the low temperature side heating medium being configured to be cooled by the high temperature side heating medium in the cascade condenser, while the brine being configured to be cooled by the low temperature side heating medium in the evaporator; and
the control apparatus is configured to control the cooling unit and the heating unit so as to control a temperature inside the chamber within a temperature zone of between −67.5° C. and 127.5° C.

2. The environmental testing apparatus according to claim 1, wherein
an internal volume of the chamber is not less than 10 m³ and not more than 20 m³.

3. The environmental testing apparatus according to claim 2, wherein:
a part of the brine circulation path, which is located in the chamber, includes a plurality of pipe parts each of which extends along the same direction; and
when seen in a section perpendicular to an extension direction of the pipe part, the plurality of pipe parts are disposed in a staggered arrangement.

4. The environmental testing apparatus according to claim 2, wherein when the brine circulation apparatus cools the space in the chamber, the brine circulation apparatus is configured to cool the space in the chamber at a cooling capacity of 4 kW, by circulating the brine in the brine circulation path at a flow rate within a range of between 80 L/min and 160 L/min.

5. The environmental testing apparatus according to claim 4, wherein:
a part of the brine circulation path, which is located in the chamber, includes a plurality of pipe parts each of which extends along the same direction; and
when seen in a section perpendicular to an extension direction of the pipe part, the plurality of pipe parts are disposed in a staggered arrangement.

6. The environmental testing apparatus according to claim 1, wherein:
a part of the brine circulation path, which is located in the chamber, includes a plurality of pipe parts each of which extends along the same direction; and
when seen in a section perpendicular to an extension direction of the pipe part, the plurality of pipe parts are disposed in a staggered arrangement.

7. The environment device apparatus according to claim 6, wherein:
the part of the brine circulation path, which is located in the chamber, is composed of a first pipe group and a second pipe group;
each of the first pipe group and the second pipe group includes the plurality of pipe parts;
the first pipe group is located on one horizontal side in the chamber, while the second pipe group is located the other horizontal end in the chamber; and
the installation space for the object to be tested is formed between the first pipe group and the second pipe group.

8. The environmental testing apparatus according to claim 7, wherein
in the chamber, a first cover member that covers the first pipe group from the installation space side is located, and a second cover member that covers the second pipe group from the installation space side is located.

9. The environmental testing apparatus according to claim 8, wherein:
a fan is located above the installation space in the chamber;
a third cover member that covers the fan from the installation space side is located in the chamber; and
the fan is configured to blow air toward the third cover member.

10. The environmental testing apparatus according to claim 9, wherein
the heater is located above the fan.

11. An environmental testing apparatus comprising:
a chamber that accommodates an object to be tested;
a cooling unit and a heating unit, which are for controlling a temperature in the chamber; and
a control apparatus that controls the cooling unit and the heating unit;
wherein:
the cooling unit includes a low temperature side refrigerating apparatus and a low temperature side brine circulation apparatus;
the low temperature side refrigerating apparatus constituting a binary refrigerating apparatus includes:
a first low temperature side refrigerating circuit in which a first low temperature side compressor, a first low temperature side condenser, a first low temperature side expansion valve and a first low temperature side evaporator are connected in this order so as to circulate a first low temperature side coolant; and a second low temperature side refrigerating circuit in which a second low temperature side compressor, a low temperature side condenser, a second low temperature side expansion valve and a second low temperature side evaporator are connected in this order so as to circulate a second low temperature side coolant; with the first low temperature side condenser and the second low temperature side evaporator constituting a cascade condenser in which they are heat-exchanged with each other;
the low temperature side brine circulation apparatus includes:
a low temperature side brine circulation path for circulating a low temperature side brine; and a low temperature side heating part constituting a part of the low temperature side brine circulation path and capable of heating the low temperature side brine received therein;
a part of the low temperature side refrigerating circuit, which is located on the downstream side of the first low temperature side expansion valve and on the upstream side of the first low temperature side evaporator, and a part of the low temperature side brine circulation path, which is located on the downstream side of the low temperature side heating part, constituting a refrigerating capacity adjusting mechanism in which they are heat-exchanged with each other; and
the first low temperature side evaporator being located in the chamber; and
the control apparatus is configured to control the cooling unit and the heating unit so as to control a temperature inside the chamber within a temperature zone of between −67.5° C. and 127.5° C.

12. The environmental testing apparatus according to claim 11, wherein:
the heating unit includes a heating side refrigerating apparatus and a heating side brine circulation apparatus;
the heating side refrigerating apparatus includes:
a heating side refrigerating circuit in which a heating side compressor, a heating side condenser, a heating side expansion valve and a heating side evaporator are connected in this order so as to circulate a heating side coolant;
an injection circuit including: an injection flow path that communicates a part of the heating side refrigerating circuit, which is located on the downstream side of the heating side condenser and on the upstream side of the heating side expansion valve, and a part of the heating side refrigerating circuit, which is located on the downstream side of the heating side evaporator and on the upstream side of the heating side compressor, such that the heating side coolant can flow therethrough; and an injection valve capable of adjusting a flow rate of the heating side coolant; and
a hot gas circuit including: a hot gas flow path that communicates a part of the heating side refrigerating circuit, which is located on the downstream side of the heating side compressor and on the upstream side of the heating side condenser, and a part of the injection flow path, which is located on the downstream side of the injection valve, such that the heating side coolant can flow therethrough; and a hot gas valve capable of adjusting a flow rate of the heating side coolant flowing through the hot gas flow path; and
the heating side brine circulation apparatus includes:

a heating side brine circulation path for circulating a heating side brine; a heating unit side heating part constituting a part of the heating side brine circulation path and capable of heating the heating side brine received therein; and a loading part constituting a part of the heating side brine circulation path on the downstream side of the heating unit side heating part and located in the chamber;

a part of the heating side brine circulation path and the heating side evaporator of the heating side refrigerating apparatus constituting a heating capacity adjusting heat exchanger in which they are heat-exchanged with each other.

13. The environmental testing apparatus according to claim 12, wherein
    the first low temperature side evaporator includes a first evaporator located on one horizontal side in the chamber, and a second evaporator located on the other horizontal side in the chamber;
    the loading part located in the chamber is composed of a first loading part located on one horizontal side in the chamber, and a second loading part located on the other horizontal side in the chamber;
    an installation space for the object to be tested is formed between the first evaporator and the first loading part, and the second evaporator and the second loading part; and
    the first evaporator is located above the first loading part, while the second evaporator is located above the second loading part.

14. The environmental testing apparatus according to claim 13, wherein
    in the chamber, a first cover member that covers the first evaporator and the first loading part from the installation space is located, and a second cover member that covers the second evaporator and the second loading part from the installation space is located.

15. The environmental testing apparatus according to claim 14,
    a fan is located above the installation space in the chamber;
    a third cover member that covers the fan from the installation space side is located in the chamber; and
    the fan is configured to blow air toward the third cover member.

* * * * *